United States Patent [19]
Pierschbacher et al.

[11] Patent Number: 5,759,855
[45] Date of Patent: Jun. 2, 1998

[54] METHODS FOR MODIFYING THE BINDING ACTIVITY OF CELL ADHESION RECEPTORS

[75] Inventors: Michael D. Pierschbacher, San Diego; John J. Grzesiak, Cardiff, both of Calif.; Daniel Kirchhofer, Obervil, Switzerland

[73] Assignee: La Jolla Cancer Research Foundation, La Jolla, Calif.

[21] Appl. No.: 104,335

[22] Filed: Aug. 9, 1993

Related U.S. Application Data

[60] Division of Ser. No. 857,058, Mar. 23, 1992, abandoned, which is a continuation-in-part of Ser. No. 701,766, May 17, 1991, abandoned, which is a continuation of Ser. No. 244,701, Sep. 14, 1988, abandoned.

[51] Int. Cl.$^6$ .............................. C12N 5/06; A01N 59/06; A61K 33/06
[52] U.S. Cl. .................... 435/325; 424/600; 424/678; 424/681; 435/334; 514/492
[58] Field of Search .................... 530/395, 356, 530/380, 350; 514/2, 8, 21, 492; 435/244, 325, 334, 337; 424/600, 678, 681, 682

[56] References Cited

U.S. PATENT DOCUMENTS

| | | |
|---|---|---|
| 4,578,079 | 3/1986 | Ruoslahti et al. |
| 4,614,517 | 9/1986 | Rouslahti et al. |
| 4,683,291 | 7/1987 | Zimmerman et al. |
| 4,853,220 | 8/1989 | Clemmensen et al. .................. 424/101 |
| 5,019,646 | 5/1991 | Furcht et al. ............................ 530/326 |
| 5,064,942 | 11/1991 | Clemmensen et al. .................. 530/387 |

OTHER PUBLICATIONS

Erkki Ruoslahi and Michael D. Pierschbacher, New Perspective in Cell Adhesion: RGD and Integrins, Science, 238:491–497 (1987).

Staatz et al., "The Membrane Glycoprotein Ia–IIa (VLA–2) Complex Mediates the Mg++–dependent Adhesion of Platelets to Collagen" *J. Cell. Biol.* 108:1917–1924 (1989).

Banai et al., "Influence of Extracellular Magnesium on Capillary Endothelial Cell Proliferation and Migration" *Circ. Res.* 67:645–650 (1990).

Marlin and Springer, "Purified Intercellular Adhesion Molecule–1 (ICAM–1) Is a Ligand for Lymphocyte Function–Associated Antigen 1 (LFA–1)" *Cell* 51:813–819 (1987).

Loftus et al., "A β3 Integrin Mutation Abolishes Ligand Binding and Alters Divalent Cation–Dependent Conformation" *Science* 249:915–918 (1990).

Sank et al., "Increased calcium levels alter cellular and molecular events in wound healing" *Surg.* 106:1141–1148 (1989).

Dransfield and Hogg, "Regulated expression of Mg2+ binding epitope on leukocyte integrin α subunits" *EMBO J.* 8:3759–3765 (1989).

Kirchhofer et al., "Calcium as a Potential Physiological Regulator of Integrin–mediated Cell Adhesion" *J. Biol. Chem.* 266:4471–4477 (1991).

Rubin et al., "Adhesion of rat hepatocytes to collagen" *Exp. Cell Res.* 117:165–177 (1978).

Smith and Cheresh, "Labeling of Integrin $\alpha_v\beta_3$ with $^{58}$Co(III)" *J. Biol. Chem.* 266:11429–11432 (1991).

Parise and Phillips, "Fibronectin–binding Properties of the Purified Platelet Glycoprotein IIb–IIIa Complex" *J. of Biol. Chem.* 261:14011–14017 (1986).

Dedhar et al., "A Cell Surface Receptor Complex for Collagen Type I Recognizes the Arg–Gly–Asp Sequence" *J. Cell. Biol.* 104:585–593 (1987).

Phillips et al., "The Platelet Membrane Glycoprotein IIb–IIIa Complex" *Blood* 71:831–843 (1988).

Springer, T.A., "Adhesion receptors of the immune system" *Nature* 346:425–434 (1990).

Buck, C.A., "Cell surface receptors for extracellular matrix molecules" *Ann. Rev. Cell Biol.* 3:179–205 (1987).

Lam et al., "Evidence That Arginyl–Glycyl–Aspartate Peptides and Fibrinogen τ Chain Peptides Share a Common Binding Site on Platelets" *J. Biol. Chem.* 262(3):947–950 (1987).

Sonnenberg et al., "Laminin receptor on platelets is the integrin VLA–6" *Nature* 336:487–489 (1988).

Lampugnani et al., "Role of Manganese in MG-63 Osteosarcoma Cell Attachment to Fibrinogen and von Willebrand Factor" *Lab. Invest.* 65:96–103 (1991).

Fujimura and Phillips, "Calcium Cation Regulation of Glycoprotein IIb–IIIa Complex Formation in Platelet Plasma Membranes" *J. Biol. Chem.* 258:10247–10252 (1983).

Phillips and Baughan, "Fibrinogen Binding to Human Platelet Plasma Membranes" *J. Biol. Chem.* 258:10240–10246 (1983).

Fitzgerald and Phillips, "Calcium Regulation of the Platelet Membrane Glycoprotein IIb–IIIa Complex" *J. Biol. Chem.* 260:11366–11374 (1985).

Pytela et al., "Identification and Isolation of a 140 kd Cell Surface Glycoprotein with Properties Expected of a Fibronectin Receptor" *Cell* 40:191–198 (1985).

Pytela et al., "A 125/115-kDa cell surface receptor specific for vitronectin interacts with the arginine–glycine–aspartic acid adhesion sequence derived from fibronectin" *PNAS USA* 82:5766–5770 (1985).

Pytela et al., "Platelet Membrane Glycoprotein IIb/IIIa: Member of a Family of Arg–Gly–Asp–Specific Adhesion Receptors" *Science* 231:1559–1561 (1986).

Pidard et al., "Temperature–Dependent Effects of EDTA on the Membrane Glycoprotein IIb–IIIa Complex and Platelet Aggregability" *Blood* 67:604–611 (1986).

Jennings and Phillips, "Purification of Glycoproteins IIb and III from Human Platelet Plasma Membranes and characterization of a Calcium–dependent Glycoprotein IIb–III Complex" *J. Biol. Chem.* 257:10458–10463 (1982).

Edwards, J.G. et al., Induction of Fibroblast Spreading by $Mn^{2+}$: a Possible Role for Unusual Binding Sites for Divalent Cations in Receptors for Proteins Containing Arg–Gly–Asp., J. Cell Sci., 89:507–513 (1988).

Edwards, J.G. et al., A Major Difference Between Serum and Fibronectin in the Divalent Cation Requirement for Adhesion and Spreading of BHK21 Cells, J. Cell Sci. 87:657–665 (1987).

Bauvois, B. and Roth, S., Initial Adhesion of Murine Fibroblasts to Collagen and Fibronectin occurs by Two Mechanisms, Cell Biochemistry and Function 5:281–287 (1987).

Santoro, S.A., Identification of a 160,000 Dalton Platelet Membrane Protein that Mediates the Initial Divalent Cation–Dependent Adhesion of Platelets to Collagen, Cell 46:913–920 (1986).

Parise, L. and Phillips, D., Reconstitution of the Purified Platelet Fibrinogen Receptor, J. of Biol. Chem. 260:10698–10707 (1985).

Stenn, K. and Core, N., Cation Dependence of Guinea Pig Epidermal Cell Spreading, In Vitro Cell and Develop. Biol. 22:217–222 (1986).

Shadle P. et al., Platelet–Collagen Adhesion: Inhibition by a Monoclonal Antibody That Binds Glycoprotein IIb., J. of Cell. Bio. 99:2056–2060.

Grinnel P., Manganese–Dependent Cell–Substratum Adhesion, J. Cell Sci. 65:61–72, (1984).

Evans, P.M. and Jones, B.M., $Mn^{2+}$–Stimulated Adhesion and Spreading of Ehrlich Ascites Cells Are Separate Processes, Cell Biol. Int. Rep. 6:681–685.

Martz, E., Immune T Lymphocyte to Tumor Cell Adhesion, J. Cell Bio. 84:584–598 (1980).

Hoover, R.L. et al., Adhesion of Leukocytes to Endothelium: Roles of Divalent Cations, Surface Charge, Chemotactic Agents and Substrate, J. Cell Sci. 45:73–86 (1980).

Klebe, R.J. et al., Cell Attachment to Collagen; The Ionic Requirements, Exp. Cell Res. 110:419–425 (1977).

Ueda, M.J. and Takeichi, M., Two Mechanisms in Cell Adhesion Revealed by Effects of Divalent Cations, Cell Structure and Function 1:377–388 (1976).

Vosbeck, K. and Roth, S., Assay of Intercellular Adhesiveness using Cell–Coated Sephadex Beads as Collecting Particles, J. Cell Sci. 22:657–670 (1976).

Maroudas, N.G., Adhesion and Spreading of Cells on Charged Surfaces, J. Theor. Biol. 49:417–424 (1975).

Allen, A. and Minnikin, S.M., The Adhesion of Baby–Hamster Kidney Cell to Glass Surfaces Coated with Glycoproteins, Biochemical Society Trans. 3:1103–1105 (1975).

Edwards, J.G. et al., Trypsinized BHK21 Cells Aggregate in the Presence of Metabolic Inhibitors and in the Absence of Divalent Cations., J. Cell Sci. 19:653–667 (1975).

Okada, T.S., et al., The Role of Divalent Cations in Cell Adhesion, Advan. in Biophys. 6:157–181 (1974).

Klebe, R.J., Isolation of a Collagen–Dependent Cell Attachment Factor, Nature 250:248–251 (1974).

Rabinovitch, M. and DeStefano, M.J., Manganese Stimulates Adhesion and Spreading of Mouse Sarcoma I Ascites Cells, J. Cell Biol. 59:165–176 (1973).

Garvin, J.E., Effects of Divalent Cations of Adhesiveness of Rat Polymorphonuclear Neutrophils In Vitro, J. Cell Physiol. 72:197–212 (1969).

Lipson, S. et al., Multivalent Cations and Cell Adhesion, Clinical Research 13:237 (1965).

Gailit, J. and Ruoslahti, E., Regulation of the Fibronectin Receptor Affinity by Divalent Cations, The Journal of Biological Chemistry 263:12927–12932 (1988).

Ignatius, M.J. and Reichardt, L.F., Identification of a Neuronal Laminin Receptor: An M 200K/120K Integrin Heterodimer that Binds Laminin into a Divalent Cation–Dependent Manner, Neuron 1:713–725 (1988).

Grzesiak et al (1992) J. Cell. Biol. 117(5):1109–17.

Rubin et al. (1978) Experimental Cell Res. 117:165–77.

Grzesiak et al. (1995) J. Clin. Invest. 95:227–233.

Leavesley et al. (1993) J. Cell Biol. 121:163–170.

*Primary Examiner*—Ponnathapura Achutamurthy
*Attorney, Agent, or Firm*—Campbell & Flores LLP

[57] ABSTRACT

The invention relates to the regulatory role of cations on the dynamics of integrin-mediated cell adhesion and migration. In one aspect, methods of promoting or inhibiting the migration of integrin-expressing cells are provided by controlling the amount of cations, such as $Mg^{2+}$ or $Ca^{2+}$, in contact with the integrins of the cells. Methods of modifying the binding avidity of an integrin for its ligand are also provided by regulating the concentration of cations in contact with the integrin. The invention further relates to methods of using cations for a variety of applications and in particular for promoting wound healing.

7 Claims, 10 Drawing Sheets

5,759,855

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:1:

```
Gly  Arg  Gly  Asp  Ser  Pro  Ala  Ser  Ser  Lys
1                 5                        10
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:2:

```
Gly  Arg  Gly  Asp  Ser  Pro  Lys
1                 5
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:3:

```
Gly  Arg  Gly  Asp  Ser  Pro
1                 5
```

( 2 ) INFORMATION FOR SEQ ID NO:4:

```
    ( i ) SEQUENCE CHARACTERISTICS:
            ( A ) LENGTH: 4 amino acids
            ( B ) TYPE: amino acid
            ( D ) TOPOLOGY: linear ( i x ) FEATURE:
            ( A ) NAME/KEY: Modified-site
            ( B ) LOCATION: 1
            ( D ) OTHER INFORMATION: /note="X=Glu/Asp"

( i x ) FEATURE:
            ( A ) NAME/KEY: Modified-site
            ( B ) LOCATION: 2
            ( D ) OTHER INFORMATION: /note="X=ANY AMINO ACID"

( i x ) FEATURE:
            ( A ) NAME/KEY: Modified-site
            ( B ) LOCATION: 3
            ( D ) OTHER INFORMATION: /note="X=ANY AMINO ACID"

( i x ) FEATURE:
            ( A ) NAME/KEY: Modified-site
            ( B ) LOCATION: 4
            ( D ) OTHER INFORMATION: /note="X=Glu/Asp"

( x i ) SEQUENCE DESCRIPTION: SEQ ID NO:4:

Xaa   Xaa   Xaa   Xaa
    1
```

METHODS FOR MODIFYING THE BINDING ACTIVITY OF CELL ADHESION RECEPTORS

This application is a division of U.S. Ser. No. 07/857,058 filed Mar. 23, 1992, abandoned which is a continuation-in part of U.S. Ser. No. 07/701,766, filed May 17, 1991, abandoned, which is a continuation of U.S. Ser. No. 07/244,701, filed Sep. 14, 1988, abandoned which are incorporated herein by reference in their entirety.

The present invention was supported in part by Grant No. HL38417 from the National Heart Lung and Blood Institute and Cancer Center Support Grant No. CA30199 from the National Cancer Institute, National Institutes of Health. The Government may have certain rights to this invention.

BACKGROUND OF THE INVENTION

Cell adhesion plays a critical role in the maintenance and promotion of cell anchorage, polarity, migration and differentiation. Adhesion processes are mediated by cell surface receptors that specifically recognize and bind to adhesion ligands.

Many of the known adhesion receptors belong to a family of receptors called integrins. The integrin family includes receptors for fibronectin, vitronectin, collagens and fibrinogen as well as receptors for von Willebrand factor, laminin, complement component C3bi and cell-cell adhesion receptors. The integrins are heterodimeric membrane proteins with large extracellular domains and small cytoplasmic tails. The ligand proteins of those integrins with known ligands share the common feature of containing the tripeptide Arg-Gly-Asp (RGD) as an essential component.

The regulation of integrin function is not well understood, but existing data indicate that the binding specificity and activity might be controlled by various means, including phosphorylation, RNA splicing, the membrane lipid environment, and by other post-translational modifications. Growth factors have been shown to regulate integrin expression. The binding function of some integrins can also be activated or increased by agonists, such as adenosine diphosphate (ADP) and thrombin for GPIIb-IIIa or ADP and phorbol esters for CD11b/CD18. The ability to manipulate such process has enormous potential applications.

A common characteristic of all integrins is the requirement for divalent cations, such as $Ca^{2+}$ and $Mg^{2+}$, to maintain binding function. These cations presumably exert their effects by binding to the three to five putative cation-binding domains located on all integrin a subunits as described in Argraves et al., *J. Cell Biol.* 105:1183–1190 (1987), and possibly by interacting directly with β subunits as described in Loftus et al., *Science* 249:915–918 (1990). The a subunits of the receptors contain several short amino acid sequences that are similar to the $Ca^{2+}$-binding sites of other known $Ca^{2+}$-binding proteins.

It has been shown that the collagen receptor on platelets, $\alpha_2\beta_1$, exhibits the same $Ca^{2+}$-inhibitable binding characteristics as $\alpha_v\beta_1$ according to Staatz et al., *J. Cell Biol.* 108:1917–1924 (1989). In addition, $Mg^{2+}$-dependent, $\alpha_2\beta_1$-mediated adhesion of platelets to collagen has also been shown to be inhibited by $Ca^{2+}$ as described in Santoro, *Cell* 46:913–920 (1986). One of the integrins mediating adhesion to collagen on fibroblasts is also very similar to that found on platelets (Kunicki et al., *J. Biol. Chem.* 263:4516–4519 (1988)). However, depending on the cell type on which it is expressed, this receptor may display altered ligand specificity according to various published reports (Languino et al.,

*J. Cell Biol.* 109:2455–2462 (1989); Kirchhofer et al., *J. Biol. Chem.* 265:615–618 (1990); Elices and Hemler, *PNAS (USA)* 86:9906–9910 (1989); and Lotz et al., *Cell Regulation* 1:249–257 (1990)).

Because of the critical role played by cell adhesion processes, a need exists to be able to manipulate such systems further. The present invention satisfies this need and provides related advantages as well.

SUMMARY OF THE INVENTION

The present invention relates to the regulation of various functions of integrin receptors. In one aspect, the invention provides methods for modifying the ability of integrin-expressing cells to migrate by adjusting the $Mg^{2+}:Ca^{2+}$ concentration ratio in contact with the cells to enhance migration. Ratios greater than 1 are particularly useful in promoting or enhancing cell migration. Combined concentrations of $Mg^{2+}$ and $Ca^{2+}$ of less than about 4 mM are also useful in enhancing cell migration.

The invention further provides methods for modifying the binding activity of an integrin for its ligand by providing the integrin with a cation, with the preferred concentration in the range of about 0.5 mM to about 20 mM, in which the cation has an integrin binding-modifying activity. Depending on the choice of cation and integrin, the binding activity can be enhanced or inhibited.

The methods of the present invention are useful for a variety of applications. For example, the methods can be used for the purification of integrins or their ligands by increasing the binding activity of the integrins. The methods can also be used to promote wound healing in which cell migration to injured sites is desirable.

BRIEF DESCRIPTION OF THE DRAWINGS

FIG. 1 shows the effects of $Ca^{2+}$ and $Mg^{2+}$ on the attachment of receptor-containing liposomes to ligand-coated surfaces. FIG. 1A shows the results of purified receptors incorporated into $^3H$-labeled liposomes and the attachment of $\alpha_v\beta_1$-containing liposomes to fibronectin, while

FIG. 2 shows cell adhesion to surfaces coated with the synthetic peptide GRGDSPASSK (SEQ ID No. 1).

DETAILED DESCRIPTION OF THE INVENTION

Figure 1A:
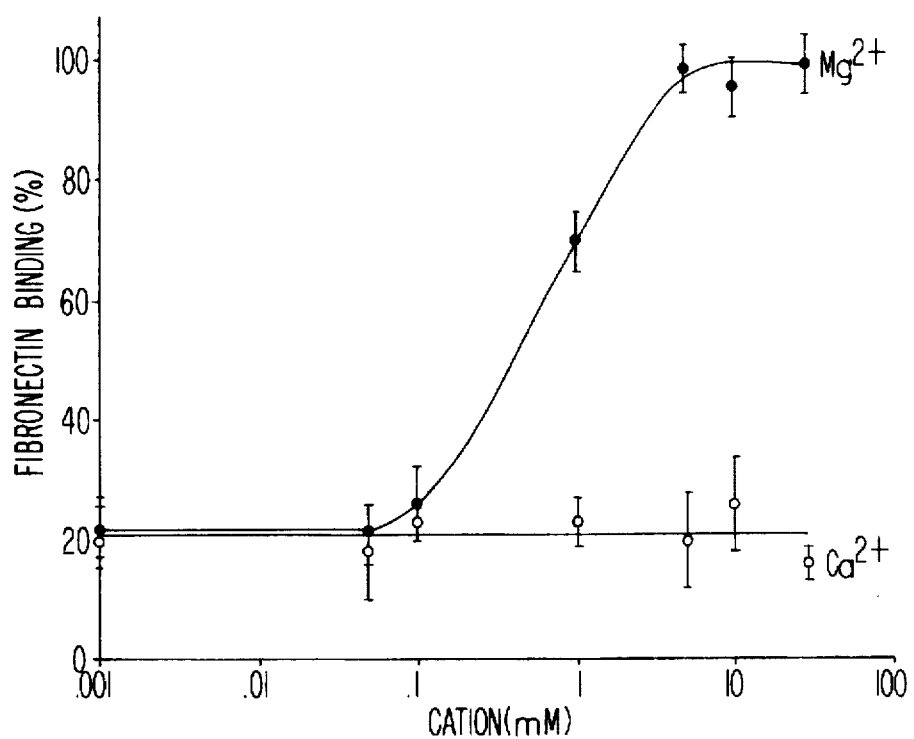

The present invention generally relates to the regulatory role of cations on the dynamics of integrin-mediated cell adhesion and migration. It has been discovered that the ability of cations to affect cell adhesion and migration can be regulated by adjusting the cation concentration in contact with various integrin-expressing cells.

The present invention accordingly provides methods for modifying the binding avidity of an integrin for its respective ligand. Such methods include providing the integrin with a cation concentration in the range of about 0.5 to 20 mM, preferably about 5 to 10 mM, whereby the cation has an integrin-binding-modifying activity. For example, the addition of $Mg^{2+}$ alone will enhance binding avidity of cells expressing $\alpha_v\beta_1$ or $\alpha_v\beta_3$, while the addition of $Ca^{2+}$ alone will enhance the binding avidity of $\alpha_v\beta_3$-expressing cells. In contrast, the addition of $Ca^{2+}$ decreases the binding activity of $\alpha_v\beta_1$-expressing cells. Other examples in which such methods can be used to regulate the functions of various integrins are provided in more detail below.

Integrins in general and their subunits are described in detail in Ruoslahti and Pierschbacher, *Science* 238:491 (1987), which is incorporated herein by reference. All terminology used herein is intended to conform to the definitions and descriptions provided by this reference. These integrins comprise a family of related cell surface heterodimeric glycoproteins that are involved in mediating cell adhesive interactions. The integrins include, but are not limited to, receptors for fibronectin, vitronectin, collagens, laminin, tenascin, and the cell surface protein IIb/IIIa that recognizes fibronectin, fibrinogen, von Willebrand factor and thrombospondin. The leukocyte adhesion receptors LFA-1, Mac-1 and gp 150/95 are also members of the integrin family of receptors. Examples of such integrins include $\alpha_v\beta_1$ (fibronectin receptor), $\alpha_v\beta_3$ (vitronectin receptor) and $\alpha_2\beta_1$ (type I collagen receptor).

For purposes of this invention, the term "cation" shall include those ions having a positive charge, preferably 2+ or 3+, such as $Ca^{2+}$ and $Mg^{2+}$. The cations useful in the present invention can also be metals and the rare earth metals such as the lanthanide series.

Cations that affect the binding activity of integrins are considered to have integrin-binding-modifying activity. Where binding activity is demonstrated by one or more assays to be increased in the presence of a cation, the cation is considered to have integrin-binding-promoting activity. Where binding activity is demonstrated by one or more assays to be decreased in the presence of a cation, the cation is considered to have integrin-binding-inhibiting activity.

As used herein, modification of receptor binding encompasses changes in binding avidity and/or changes in binding affinity. Increased binding avidity relates to an increase in the total number of receptor molecules binding to ligands. Increased binding affinity reflects an increase in the strength of binding between individual receptors and their ligands. Increased binding activity may reflect either increased binding affinity or increased binding avidity. Decreased binding avidity or affinity would be known to those skilled in the art to have the opposite meaning.

In addition, the term "integrin-expressing cell" as used herein refers to cells having integrins that can be modified by cations that affect the various binding activities of an integrin, including cell binding, adhesion or migration. Such integrins include those identified above.

The demonstration that integrin-binding-promoting cations modify binding activity of integrins has a number of applications. For example, the purification of integrins, such as on a ligand-conjugated matrix column, can be facilitated. Such column purification is described in Pytela et al., *PNAS (USA)* 82:5766–5770 (1986), which is incorporated herein by reference. Briefly, a ligand reactive with the integrin of interest is conjugated to an appropriate support matrix, such as Sepharose®. Other matrix materials known or commercially available can also be used. Such ligands include intact integrin ligands, as well as fragments thereof, such as the 110 kD fragment of fibronectin, and synthetic RGD-containing peptides. A solution containing the desired integrin is passed over the column, thereby permitting the integrin to bind to the matrix. A solution capable of detaching the bound integrin from the matrix is then passed through the column, thereby eluting any bound integrin. In the presence of appropriate integrin-binding-promoting cation in the binding solution, the amount of integrin bound to the column is increased, resulting in a greater yield of purified integrin.

Moreover, the increased integrin binding activity in the presence of integrin-binding-promoting cations facilitates assays to determine the presence of either integrins or their ligands. For example, various immunoassay formats are available for determining the presence of binding pairs, such as a receptor-ligand, using labelled antibodies reactive with either the ligand or receptor. Such methods are well known to those skilled in the art. See for example *Handbook of Experimental Immunology* (D. M. Weir, ed.) Blackwell Scientific Publications (3d ed. 1978), which is incorporated herein by reference. Appropriate labels include enzymes, components of a fluorescent, luminescent or chemiluminescent system, and radionuclides. Alternatively, a similarly labelled receptor or a labelled ligand may be utilized to determine the presence of the ligand or receptor, respectively, in the presence of integrin-binding-promoting cations.

The present invention further provides methods for modifying the migration of integrin-expressing cells by adjusting the $Mg^{2+}$:$Ca^{2+}$ concentration ratio in contact with the cells sufficient to modify the migration of the cell. Modifying cell migration includes enhancing (i.e., promoting) as well as inhibiting cell migration.

For enhancing cell migration, the ratio of $Mg^{2+}/Ca^{2+}$ is preferably greater than 1, particularly with type I collagen receptors, such as a $\alpha_2\beta_1$, for example. The preferred ratio falls within a range of about 1.5 mM/l mM to about 2 mM/l mM. In addition, a combined concentration of $Mg^{2+}$ and $Ca^{2+}$ of less than about 4 mM, and preferably in the range of about 2 mM to 3 mM, has been found useful in enhancing cell migration, particularly with $\alpha_v\beta_3$-expressing cells on vitronectin substrates.

Cell migration is also enhanced by increasing the $Ca^{2+}$ concentration in the presence of vitronectin receptors, such as $\alpha_v\beta_3$, or by increasing $Mg^{2+}$ concentration in the presence of type I collagen receptors, such as $\alpha_2\beta_1$. In contrast, cell migration is inhibited by increasing the concentration of $Ca^{2+}$ in the presence of type I collagen receptors, while $Mg^{2+}$ inhibits cell migration of receptors having vitronectin receptors, such as $\alpha_v\beta_3$.

That integrin-binding-promoting cations facilitate cell migration is particularly unexpected considering that cell migration requires both cell attachment and cell detachment. It would not be expected that factors aiding cell attachment would also aid cell migration.

Integrin-binding-promoting cations, preferably $Ca^{2+}$ or $Mg^{2+}$, can be applied directly or indirectly to the location where cell migration is desired, such as for promoting wound healing as a result of injury or burn, for instance. The cation can be administered in a number of ways, such as by application of or immersion in a solution, by injection or by providing the cation in a suitable dressing, such as a bandage or internal reservoir. For example, the cation(s) can be incorporated into wound dressings made of RGD-peptides and biodegradable polymers. Moreover, administration in conjunction with a prosthesis or transplant can facilitate migration and attachment of host cells. Slow release or prolonged release methods of administration known to those in the art can be used.

Accordingly, the present invention additionally provides methods for promoting wound healing. Such methods are accomplished by administering at least one integrin binding promoting cation, such as $Ca^{2+}$ or $Mg^2$, directly or indirectly to the site of a wound on or in a subject. The methods can be used for veterinary or medical treatment or research of wounds and can be administered as described above. The appropriate dosage can be readily determined by those skilled in the art based on a consideration of factors such as the location of the wound, mode of administration, extent of injury and the like. In addition, the choice and amount of cation(s) used will depend on the desired effects, i.e. whether the integrin activity is preferably enhanced or inhibited.

Data generated in studies relating to the present invention lend support to the effectiveness of the above methods. The studies, which are described in more detail below, were directed to determining the role of $Ca^{2+}$ and $Mg^{2+}$ in modifying the functional activity of various integrins and are reported, in part, in Kirchhofer et al., *J. Biol. Chem.* 266:4471–4477 (1991), which is incorporated herein by reference.

In determining the role that $Ca^{2+}$ and $Mg^{2+}$ play in the regulation of the binding function of two Arg-Gly-Asp (RGD) -dependent integrins, $\alpha_v\beta_1$ and $\alpha_v\beta_3$, both of which share the same $\alpha$ subunit, it has been discovered that while $\alpha_v\beta_3$ binds to ligand in either $Ca^{2+}$ or $Mg^{2+}$, $\alpha_v\beta_1$ binds only in $Mg^{2+}$ and not in $Ca^{2+}$. These cation effects were observed with isolated receptors, in affinity chromatography and in cell adhesion. It has also been found that in the presence of $Mg^{2+}$, $Ca^{2+}$ had opposite effects on these receptors in that it inhibited the ligand binding of $\alpha_v\beta_1$ but enhanced the binding of $\alpha_v\beta_3$. These results suggest a potential regulatory role for $Ca^{2+}$ in integrin-mediated cell adhesion and support the possible involvement of the $\beta$ subunit in cation binding.

Evidence for the above results was derived from studies of integrin-ligand interaction employing liposome assays with purified receptors and receptor-mediated cell adhesion. First, $Mg^{2+}$ was found to support the attachment of $\alpha_v\beta_1$-loaded liposomes to fibronectin, whereas $Ca^{2+}$ did not. In contrast, both $Ca^{2+}$ and $Mg^{2+}$ supported binding of $\alpha_v\beta_3$-loaded liposomes to the appropriate ligand, vitronectin. Second, $Ca^{2+}$ and $Mg^{2+}$ regulated the $\alpha_v\beta_1$- and $\alpha_v\beta_3$-mediated cell adhesion in a similar fashion as in liposome assays. IMR 32 cells, which exclusively adhere to RGD-containing peptides through $\alpha_v\beta_1$, failed to adhere to the GRGDSPASSK (SEQ ID NO. 1) substrate in the presence of $Ca^{2+}$. In contrast, the $\alpha_v\beta_3$-mediated adhesion of U 251 cells that lack $\alpha_v\beta_1$ bind to RGD-peptide through $\alpha_v\beta_3$ as demonstrated by the ability of $\alpha_v\beta_3$ to bind to GRGDSPK-Sepharose (SEQ ID NO. 2) in affinity chromatography experiments using extracts of surface-labeled U 251 cells. The cation concentrations for optimal binding were 5–10 mM and identical for both the receptor-liposomes and the cell adhesion system. Thus, it seems that the cell does not alter the amount of cation necessary for maximal $\alpha_v\beta_1$ and $\alpha_v\beta_3$ binding, even though membrane lipids and gangliosides have been implicated as potential modulators of the cation-dependent binding of integrins. In support of this finding, the binding pattern of $\alpha_v\beta_1$ and $\alpha_v\beta_3$ from WI 38 cells, which express both receptors, corresponded well to the liposome and cell adhesion data. Affinity chromatography experiments showed that $\alpha_v\beta_3$ but not $\alpha_v\beta_1$ bound to GRGDSPK-Sepharose (SEQ ID NO. 2) in the presence of $Ca^{2+}$, whereas the receptor binding was reversed in $Mg^{2+}$.

Although $Ca^{2+}$ alone did not provide any a $\alpha_v\beta_1$ binding, $Ca^{2+}$ in combination with $Mg^{2+}$ was tested to determine whether the effect on $\alpha_v\beta_1$ was similar to the $Ca^{2+}/Mg^{2+}$ synergism reported for the LFA-1-ICAM interaction in Marlin and Springer, *Cell* 51:813–819 (1987). Surprisingly, moderate concentrations of $Ca^{2+}$ completely inhibited the $\alpha_v\beta_1$-mediated adhesion of IMR 32 cells to the peptide substrate in the presence of 5 mM $Mg^{2+}$. Under identical conditions, $Ca^{2+}$ enhanced the $\alpha_v\beta_3$-mediated binding of U 251 cells. These data suggest that $\alpha_v\beta_1$ binds only with a small fraction of its full capacity under physiological conditions, such as at millimolar concentrations of both $Ca^{2+}$ and $Mg^{2+}$. Another integrin, the collagen receptor on platelets, $\alpha_2\beta_1$, shows similar $Ca^{2+}$-inhibitable binding characteristics as $\alpha_v\beta_1$, and the $\alpha_2\beta_1$-mediated adhesion of platelets to collagen is also reduced by the addition of $Ca^{2+}$. Thus, it seems that the $Ca^{2+}$-dependent suppression and enhancement of binding activity is more widespread in the integrin family and suggests the possibility of a true regulatory role for localized $Ca^{2+}$ flux in controlling this binding.

The results from the liposome assays and the cell adhesion experiments consistently show that the most pronounced increases in the binding activity of $\alpha_v\beta_1$ occur at about 0.5–2 mM $Mg^{2+}$. Pronounced increases in the binding activity of $\alpha_v\beta_3$ similarly occur at about 0.5–2 mM $Ca^{2+}$ or $Mg^{2+}$. These concentrations are close to the range of their physiological concentrations. Thus, under physiological cation conditions, small changes in the cation concentrations could result in significant increases or decreases of integrin binding.

Moreover, in the presence of $Mg^{2+}$, small changes in the $Ca^{2+}$ concentration are sufficient to cause dramatic changes in integrin binding. The observation that an increase in the $Ca^{2+}$ concentration results in the suppression of $\alpha_v\beta_1$ binding, but in an enhancement of $\alpha_v\beta_3$ binding also suggests that in a $Ca^{2+}$-rich environment the binding activity of $\alpha_v\beta_1$, and thus $\alpha_v\beta_1$-mediated adhesion to fibronectin, will be virtually absent. However, cells having multiple integrin receptors could still bind to vitronectin via $\alpha_v\beta_3$. Because integrins are integral membrane proteins presumably capable of transmitting signals across the cell membrane, cation-dependent changes in the binding activity of a particular integrin might result in a different set of signals being transmitted to the cell even if a full complement of integrins was present on the surface of that cell.

The binding sites for $Ca^{2+}$ and $Mg^{2+}$ on $\alpha_v\beta_1$ and $\alpha_v\beta_3$ are believed to reside in several short domains on the $\alpha_v$ subunit according to Suzuki, et al., *J. Biol. Chem.* 263:18726–18731 (1988), with sequence similarities to the classical $Ca^{2+}$-binding proteins parvalbumin and calmodulin described in Kretsinger, *Ann. Rev. Biochem.* 45:239–266 (1976). In support of this idea, others have demonstrated that [$^{45}$Ca] binds to the a subunit of $\alpha_v\beta_3$ (Gailit and Ruoslahti, *J. Biol. Chem.* 263:12927–12932 (1988)). Although $\alpha_v\beta_1$ and $\alpha_v\beta_3$ share a common a subunit, the present results show that the two receptors prefer different cations for binding to their ligands and respond in an inverse manner to $Ca^{2+}$ in the presence of $Mg^{2+}$. A possible explanation could be that the $\beta$ subunits are in some way participating in the cation binding. Neural-crest cell migration is purportedly a $\beta_1$-integrin mediated event according to Lallier & Bronner-Fraser, *Development* 113:1069–1084 (1991).

Conversely, the $\beta$ subunits are involved in forming the ligand-binding site. Therefore, $Ca^{2+}$ binding to the $\alpha_v$ subunit may affect the ligand binding differently due to the different structures of the $\beta_1$ and $\beta_3$ subunits. Although it is possible that the ligand is involved, $Ca^{2+}$ has different effects on the binding of $\alpha_v\beta_1$ and $\alpha_v\beta_3$ to the same RGD-containing peptide, which itself does not appear to bind calcium, suggests that the receptor rather than the ligand determines the $Ca^{2+}$ effect.

The $\beta$ subunit might be involved in cation binding either by interacting with the binding sites on the $\alpha$ subunits or by binding cations itself. Putative cation-binding sites on the $\beta1$ and $\beta_3$ subunits might be formed by clusters of acidic amino acids. Analogous to the proposed auxiliary cation-binding sites on calmodulin, several Glu/Asp-X-X-Glu/Asp (SEQ ID No. 4) sequences are located in both $\beta1$ and $\beta_3$ in domains that, according to secondary structure predictions by the method of Garnier et al., *J. Mol. Biol.* 120:97–120 (1978), would be predicted to have $\alpha$-helical structure. Four such clusters have been identified in the $\beta_1$ subunit ($Asp^{65}$-$Glu^{68}$, $Asp^{157}$-$Glu^{160}$, $Glu^{452}$-$Glu^{455}$, and $Glu^{510}$-$Asp^{513}$) and five in the $\beta_3$ subunit ($Glu^{52}$-$Glu^{55}$, $Asp^{361}$-$Glu^{364}$, $Glu^{613}$-$Glu^{616}$, $Asp^{637}$-$Glu^{640}$, and $Glu^{644}$-$Asp^{647}$). Such additional cation-binding sites might account for the different $Ca^{2+}$ effects on $\alpha_v\beta_1$ and $\alpha_v\beta_3$. A model that might equally well accommodate our findings was recently proposed by Loftus et al., supra. It was suggested that a conserved 12 amino acid sequence on the integrin B subunits starting at $Asp^{119}$ in $\beta_3$ might coordinate divalent cations. According to this model the different effects of $Ca^{2+}$ on $\alpha_v\beta_1$ and $\alpha_v\beta_3$ could be attributed to differences in the amino acid sequences of the corresponding binding sites or the surrounding sequences on the $\beta_1$ and $\beta_3$ subunits.

Alternatively, the $\beta$ subunit might participate in forming cation binding sites in conjunction with the proposed cation-binding sequences on the $\alpha$ subunit.

Although similar to the $Ca^{2+}$-binding loops of calmodulin and parvalbumin, these amino acid sequences on the $\alpha$ subunits were noticed to be more closely related to $\alpha$ bacterial galactose-binding protein described in Edwards et al., *J. Cell Sci.*, 89:507–513 (1988). Calmodulin and parvalbumin consistently have a glutamic acid residue at position 12 (coordination site-Z) in the $Ca^{2+}$-binding loop, whereas the corresponding sequence in the galactose-binding protein and in all known integrin $\alpha$ subunits have a hydrophobic residue in this position except for a serine in one of the sequences in $\alpha_v$ (see Table I of Kirshhofer et al, (1991), supra). Therefore, it is possible that analogous to the galactose-binding protein, a distant glutamic acid on the $\alpha$ subunit might loop into the cation-binding site and provide the sixth coordination site (–Z), forming the so-called lock washer structure as described in Edwards et al., (1988), supra. Following this model, the glutamic acid residue might be provided by the β subunit and that the different structures of the $\beta_1$ and $\beta_3$ subunit might account for the different cation requirements and $Ca^{2+}$ effects of $\alpha_v\beta_1$ and $\alpha_v\beta_3$.

The role of $Ca^{2+}$ as a regulator of the binding function of two related RGD-dependent integrins, $\alpha_v\beta_1$ and $\alpha_v\beta_3$ has been demonstrated. The $Ca^{2+}$-dependent inhibition of $\alpha_v\beta_1$ and the enhancement of $\alpha_v\beta_3$ binding function in the presence of $Mg^{2+}$ occurred at physiological cation concentrations in the cell adhesion test systems suggesting a physiologically relevant role for $Ca^{2+}$. Because the binding function of another integrin, $\alpha_2\beta_1$, is also inhibited by $Ca^{2+}$ (Staatz et al., supra and Santoro, supra), it might be that $Ca^{2+}$, by its ability to suppress or enhance the binding function of a set of integrins on a given cell, could regulate cell behavior either by changing adhesive properties of the cell or by influencing the transmembrane signaling mediated by the integrin receptors. An intriguing example of an adhesive mechanism which is affected by significant changes in the $Ca^{2+}$ concentration is the interaction of osteoblasts with the extracellular matrix during bone resorption. It seems possible that the reduction in the bone resorptive activity of osteoblasts that is induced by elevated extracellular $Ca^{2+}$ concentrations might be, at least in part, due to the effect of calcium on the function of integrins such as $\alpha_v\beta_3$, which binds to bone sialoprotein and has been implicated in the regulation of bone resorption.

The potential regulatory role of extracellular $Ca^{2+}$ and $Mg^{2+}$ on the dynamics of the $\alpha_2\beta_1$-mediated migration of fibroblasts on type I collagen was also examined. The results presented herein suggest that integrin-mediated fibroblast migration on type I collagen can be regulated, at least in part, by small fluctuations in divalent cation concentration. Fibroblastic cells that express both $\alpha_2\beta_1$ and $\alpha_v\beta_3$ exhibited migration in the presence of $Mg^{2+}$ on type I collagen, but not on the control, vitronectin, in the presence of $Mg^{2+}$, while in the presence of $Ca^{2+}$, cells migrate on vitronectin but not type I collagen. Furthermore, migration on collagen is significantly enhanced when both cations are present, but is optimal when the ratio of $Mg^{2+}/Ca^{2+}$ concentration is higher than 1. Monoclonal antibodies directed against the $\alpha_2$ and $\beta_1$ integrin subunits inhibit this migration on type I collagen, suggesting that these observed cation effects are mediated through $\alpha_2\beta_1$. These data suggest a possible physiological role for the divalent cations, $Mg^{2+}$ and $Ca^{2+}$, in the modulation of integrin-mediated cell migration.

In the studies of integrin-ligand interactions employing integrin-mediated cell adhesion, affinity chromatography and modified Boyden chamber migration assays demonstrate that $Ca^{2+}$ can reverse the $Mg^{2+}$-dependent, $\alpha_2\beta_1$-mediated adhesion of fibroblasts to type I collagen substrates. That WI38 cells were still capable of $Mg^{2+}$-dependent adhesion after pre-incubation with $Ca^{2+}$ alone suggests that exposure to $Ca^{2+}$ is not detrimental to the cell or receptor. $Ca^{2+}$ can specifically elute the fibroblast $\alpha_2\beta_1$ integrin from a type I collagen-Sepharose column when bound in the presence of $Mg^{2+}$. While WI38 cells migrate on type I collagen in the presence of $Mg^{2+}$ alone but not $Ca^{2+}$ alone, a combination of $Mg^{2+}$ and $Ca^{2+}$, with $Mg^{2+}$ in a slight excess, caused a two-fold enhancement of migration. Taken together, these results suggest that the relative concentrations of extracellular $Mg^{2+}$ and $Ca^{2+}$ are involved in the regulation of the function of this integrin and could influence the migratory behavior of fibroblasts. It has also been proposed that $\alpha_3\beta_1$ can be regulated by a shift in divalent cation concentration as reported in Elices et al., *J. Cell Biol.* 112:169–181 (1991). These data, together with the results demonstrating that $Ca^{2+}$ can also elute $\alpha_5\beta_1$, from ligand bound in $Mg^{2+}$, may reflect a general inhibitory effect of $Ca^{2+}$ on the function of $\beta_1$ integrins and indicate that $Mg^{2+}/Ca^{2+}$ ratios may substantially affect the binding function of $\beta_1$ integrins.

In recent studies employing $\alpha_v\beta_1$ and $\alpha_v\beta_3$, two integrins sharing a common a subunit, it was unexpectedly discovered that the two receptors function in different extracellular cation environments. Although not wishing to be bound by any particular theory, it is believed that residues on the β subunit participate with the proposed cation binding sequences on the a subunit to provide the sixth coordination site (–Z) for divalent cation binding.

Recent crystallographic studies of the cation-binding loops (EF loops or hands) in parvalbumin, demonstrate that cations with an ionic radius closest to 1 angstrom are favored thermodynamically. Those with smaller ionic radii are more constraining, and thus require more energy. Of all the physiological cations, $Ca^{2+}$ comes closest with an ionic radius of 0.94 angstroms and this accounts for its reportedly higher affinity binding in these cation binding loops. $Mg^{2+}$, however, with an ionic radius of 0.65 angstroms, also binds in these loops and crystallographic data show that the coordination spheres of parvalbumin that contain these cation-binding domains contract and become more constrained in the presence of $Mg^{2+}$ when compared to $Ca^{2+}$ as described in Declercq et al., *J. Mol. Biol.* 220:1017–1039 (1991).

If the same cation-dependent conformational changes occur in the cation-binding domains of integrins, and involvement of the β subunit in these domains is required for ligand binding, a mechanism based on fluctuations in the relative concentrations of $Mg^{2+}$ and $Ca^{2+}$, resulting in changes in the affinity of integrins, could explain how their function is up- and down-regulated during a cellular process such as migration.

Under normal physiological conditions, the extracellular environment has about a 1.5 mM higher concentration of $Ca^{2+}$ than $Mg^{2+}$. The in vitro results herein suggest that fibroblasts are capable of a certain level of $\alpha_2\beta_1$-mediated adhesion (FIG. 1A–B) and migration (FIG. 4A–B) on type I collagen under these conditions. However, the data also suggest that the potential exists for a two-fold increase in this activity when both $Ca^{2+}$ and $Mg^{2+}$ are used in a suitable ratio.

Whether sufficient $Mg^{2+}$ could be recruited to affect the extracellular $Mg^{2+}$ concentration is uncertain. The concentration of intracellular $Mg^{2+}$ in the typical mammalian cell is reported to be between 15 and 30 mM, while intracellular $Ca^{2+}$ is only about 1–2 mM. In the event of tissue injury, for example, an increase in extracellular $Mg^{2+}$ levels could occur locally as the damaged tissue releases its cellular contents. Such an increase in extracellular $Mg^{2+}$ could stimulate platelet binding to collagen through $\alpha_2\beta_1$ as described in Santoro, supra. A $Mg^{2+}$-gradient, set up locally from the site of injury, along with growth factors released from the platelet, may then provide the stimulus and directional signalling necessary to mobilize fibroblasts and other cells required for a successful wound healing process. This mechanism is consistent with the results showing that even subtle changes in this cation ratio can dramatically affect the ability of a cell to migrate on type I collagen.

Another type of regulation that could influence an integrin-mediated wound migratory response might be factors that deplete extracellular $Ca^{2+}$ levels. $Ca^{2+}$-binding proteins when released from platelets or other cells might serve locally as $Ca^{2+}$ chelators. Transmembrane $Ca^{2+}$ fluxes via voltage gated $Ca^{2+}$ channels in the plasma membrane are associated with amoeboid cell movement. A recent report described in Fujimoto et al., *J. Biol. Chem.* 266:16370–16375 (1991) also suggests that a GPIIb-IIIa complex-associated $Ca^{2+}$ channel facilitates extracellular $Ca^{2+}$ influx across the plasma membrane of platelets after thrombin stimulation. Whether resulting from increases in extracellular $Mg^{2+}$, decreases in extracellular $Ca^{2+}$, or a combination of both, alterations of the extracellular cation environment can occur. Such changes can influence the behavior of cells during an integrin-mediated migratory response.

Indirect support for such speculation has been documented, in cases of trauma, such as severe burns, spinal cord injury, and myocardial ischemia, when there is an increased requirement for extracellular $Mg^{2+}$ during recovery from these injuries, and that internal mechanisms are also established in an attempt to maintain elevated extracellular $Mg^{2+}$ levels, even at the expense of healthy adjacent tissue. A report illustrating that capillary endothelial cell proliferation and migration, both important for revascularization after trauma, are enhanced in the presence of elevated extracellular $Mg^{2+}$ as described in Banai et al., *Circ. Res.* 67:645–650 (1990) suggests that these extracellular $Mg^{2+}$ increases may provide a physiological stimulus for endothelial cell migration. The results obtained in the present studies demonstrate that the same appears to be true for fibroblasts which are a predominant cell type responsible for re-establishing the extracellular matrix in wound areas.

Support for this hypothesis is also suggested in a report demonstrating that increased extracellular $Ca^{2+}$ significantly inhibits both keratinocyte chemotaxis and adhesion on type I collagen. Using an in vivo rat model, they demonstrated further that topical $Ca^{2+}$ significantly delays wound contraction characteristic of a chronic or impaired wound, though the correlation to integrin function was not made in Sank et al., *Surg.* 106:1141–1148 (1989). However, recent inhibitory monoclonal antibody studies suggest that $\alpha_2\beta_1$ appears to be the integrin responsible for migration of the human keratinocyte cell line HaCaT on type I collagen and that integrin may account for the cation effects observed in the system described above. Finally, the leukocyte $\beta_2$ integrins appear to undergo conformational changes which stimulate their ligand binding functions. In one of these studies, a monoclonal antibody was defined which reacted with all three $\beta_2$ integrins only after leukocyte activation and only in the presence of $Mg^{2+}$ (Dransfield and Hogg, *EMBO J.* 8:3759–3767 (1989). This work raised the possibility that activation may result in integrin conformational changes that allow $Mg^{2+}$ binding or that $Mg^{2+}$ binding is required for the conformational changes to occur.

Together, these findings suggest that during injury, a resulting shift in the relative concentrations of extracellular $Ca^{2+}$ and $Mg^{2+}$ favoring $Mg^{2+}$ could facilitate and/or enhance a potential integrin mediated wound migratory response. As the injury is repaired and the extracellular environment is normalized, the entire mechanism could down-regulate, and the $Mg^{2+}$-dependent integrins would return to their normal physiologic state. Such sensitivity to even subtle changes in the ratio between these two extracellular divalent cations acts to control the migration of cells such as fibroblasts, keratinocytes, leukocytes and endothelial cells, which contribute to successful wound healing response.

The methods of the present invention also have potential therapeutic use in cancer treatment. For example, certain metastatic tumors, such as melanoma for example, have increased expression of $\alpha_v\beta_3$ integrins. Such malignancies are often accompanied by hypercalcemia, a condition regarded as a marker of malignancy. As shown in the studies disclosed above, the addition of $Ca^{2+}$ resulted in enhancing the migration of $\alpha_v\beta_3$-containing cells, while $Mg^{2+}$ inhibits migration of such cells. Therefore, it may be possible to counter the hypercalcemic condition by adding an effective amount of $Mg^{2+}$ to retard cell migration and consequent metastasis. Alternatively, methods of reducing the level of calcium would be potentially beneficial as well.

The following examples are intended to illustrate but not limit the invention.

EXAMPLE I

The following procedures were used to obtain the results discussed in Examples II through V.

A. Proteins and Peptides

Human plasma fibronectin was from the Finnish Red Cross (Helsinki, Finland), and vitronectin was purified from human plasma by monoclonal antibody affinity chromatography as described in Hayman et al., *PNAS (USA)* 80:4003–4007 (1983) and Suzuki et al., *J. Biol. Chem.* 259:15307–15317 (1984), both incorporated herein by reference. The peptides GRGDSP (SEQ ID NO. 3) and GRGDSPASSK (SEQ ID NO. 1) were synthesized in a peptide synthesizer (Applied Biosystems Inc., Foster City, Calif.) and purified by ion exchange high performance liquid chromatography.

B. Cells

Human neuroblastoma cells IMR 32 (ATCC No. CCL 127) and human lung fibroblasts WI38 (ATCC No. CCL 75) were obtained from the American Type Culture Collection (Rockville, Md.), and human glioblastoma cells U 251 have been described in Bigner et al., *J. Neuropathol. Exp. Neurol.* 40:210–229 (1981). The cells were cultured in Dulbecco's modified Eagle's medium (DME) supplemented with 10% fetal calf serum at 37° C.

C. Binding Assay of Receptor-containing Liposomes

The $\alpha_v\beta_3$ receptor was isolated from extracts of human placenta, and $\alpha_v\beta_1$ was purified from extracts of IMR 32 cells by affinity chromatography on GRGDSPK-Sepharose (SEQ ID NO. 2) according to the procedures described in Vogel et al., *J. Biol. Chem.* 265:5934–5937 (1990) and Pytela et al., *PNAS (USA)* 82:5766–5770 (1985), which are incorporated herein by reference. Liposomes were prepared according to Mimms et al. *Biochemistry* 20:388–340 (1981), incorporated herein by reference, and used in attachment assays as described in Pytela et al., *Methods Enzymol.* 144:4750489 (1987), incorporated herein by reference. Receptors and $^3$H-labeled phosphatidylcholine (Du Pont-New England Nuclear) were mixed and dialyzed extensively at 4° C. against TBS (50 mM Tris-HCl, pH 7.5, 150 mM NaCl). The liposomes were then diluted with TBS containing 2.5 mg/ml BSA. 96-well microtiter plates (Titertek, Flow Laboratories, McLean, Va.) were coated overnight at 4° C. with 10 µg/ml of vitronectin, fibronectin, and BSA. The plates were blocked with 10% non-fat milk in PBS for 6 hours at 4° C. The washed plates were incubated overnight at 4° C. with receptor-containing liposomes in the presence of various concentrations of $CaCl_2$ and $MgCl_2$. After washing with cold TBS, the bound liposomes were solubilized with 1% SDS, and the radioactivity was measured in a β-counter (Beckman, model LS 5000 CE).

D. Affinity Chromatography

Cells were detached with 3 mM EDTA and washed with PBS. The final cell pellet (0.6 ml) was resuspended in PBS and labeled with 3 mCi of $^{125}$I-sodium iodide according to the lactoperoxidase method described in Lebien et al., supra. The reaction was stopped with Dulbecco's modified Eagle's medium containing 0.02% sodium azide, and the cells were washed with cold PBS. The receptors were extracted at 4° C. for 20 minutes in TBS containing 100 mM octyl glucopyranoside and 2 mM phenylmethylsulfonyl fluoride. The lysate was centrifuged at 12,000×g for 20 minutes. The supernatant was split into two equal volumes which were supplemented either with 3 mM $CaCl_2$ or 3 mM $MgCl_2$. The supernatants were then applied on two 0.5-ml GRGDSPK-Sepharose columns prepared by coupling the peptide GRGDSPK to cyanogen bromide-activated Sepharose 4B according to manufacturer's instructions (Sigma). After 2 hours incubation, the columns were washed with 14 bed volumes of TBS containing 50 mM octyl glucopyranoside and 3 mM $CaCl_2$ or 3 mM $MgCl_2$. The receptors were eluted from the columns with 10 mM EDTA in TBS containing 50 mM octyl glucopyranoside and analyzed by SDS-polyacrylamide gel electrophoresis and autoradiography.

E. Coupling of Peptide to Polystyrene

The peptide of interest was bound to microtiter plates as described previously in Pierschbacher et al., *PNAS (USA)* 80:1224–1227 (1983) and Pierschbacher et al., *Nature* 309:30–33 (1984), both incorporated herein by reference, except that glutaraldehyde was used as a cross-linker. Briefly, 96-well microtiter plates (Titertek) were coated with 10 µg/ml of rabbit IgG (Sigma) overnight at room temperature. The plates were then washed three times with PBS, and 100 µl of 1% glutaraldehyde in PBS was added to each well. After 1 hour the wells were washed three times with PBS and incubated with 50 µg/ml of GRGDSPASSK peptide in PBS or with PBS only (controls) for 4 hours at room temperature. Unoccupied sites were blocked by incubating overnight with 1M ethanolamine containing 2.5 mg/ml BSA.

F. Cell Attachment Assay

The IMR 32 cell attachment assays were performed according to the procedures described in Ruoslahti et al., *Methods Enzymol.* 82:803–831 (1982), incorporated herein by reference. Briefly, $1.5 \times 10^5$ IMR 32 or $1.0 \times 10^5$ U 251 cells in 100 µl of TBS containing 2.5 mg/ml BSA were added to each well of microtiter plates (Titertek) which were coated with 50 µg/ml GRGDSPASSK (SEQ ID NO. 1) peptide. Various concentrations of $CaCl_2$ or $MgCl_2$ were added to each well and mixed with the cells. After 1 hour of incubation at 37° C., the unattached cells were washed away and attached cells were fixed with 3% paraformaldehyde in PBS. The cells were then stained with 0.5% toluidine blue in 3.7% formaldehyde, solubilized with 2% SDS, and the absorbance at 600 nm was measured in a vertical pathway spectrophotometer.

EXAMPLE II

Figure 1B:
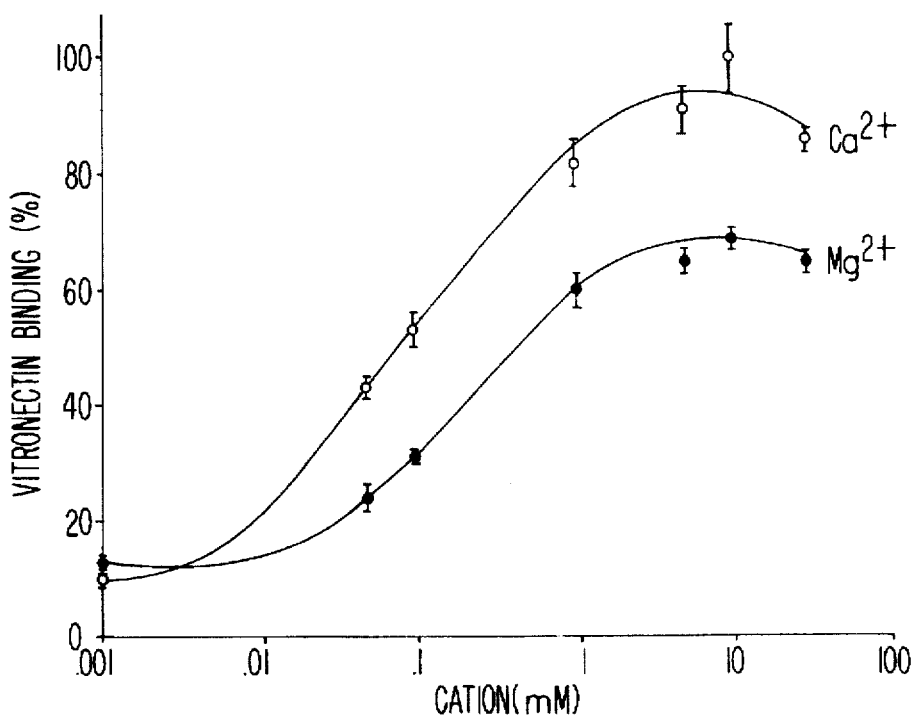
FIG. 1B shows the attachment of $\alpha_v\beta_3$-containing liposomes to vitronectin, both in the presence of increasing concentrations of $Ca^{2+}$ and $Mg^{2+}$. Non-specific binding to BSA was subtracted from each value. The results represent the mean ±S.D. of three experiments.

Effects of $Ca^{2+}$ and $Mg^{2+}$ on the Ligand Binding of Purified $\alpha_v\beta_1$ and $\alpha_v\beta_3$ Integrins To study the effects of divalent cations on RGD-dependent integrin binding, $\alpha_v\beta_3$ was isolated from IMR 32 cells and $\alpha_v\beta_3$ from human placenta by affinity chromatography on GRGDSPK-Sepharose (SEQ ID NO. 2). The receptors were then incorporated into 3H-labeled liposomes, and the attachment of $\alpha_v\beta_1$ and $\alpha_v\beta_3$ to surfaces coated with fibronectin and vitronectin, respectively, was determined. As shown in FIG. 1A, $\alpha_v\beta_1$ did not bind significantly to its ligand, fibronectin, in $Ca^{2+}$ but bound well in $Mg^{2+}$. However, $\alpha_v\beta_3$ bound well in the presence of both $Ca^{2+}$ and $Mg^{2+}$ reaching maximal binding at a concentration of 5–10 mM for both cations (FIG. 1B). Higher cation concentrations in the liposome assays significantly decreased liposome binding in all cases.

EXAMPLE III

Figure 2A:
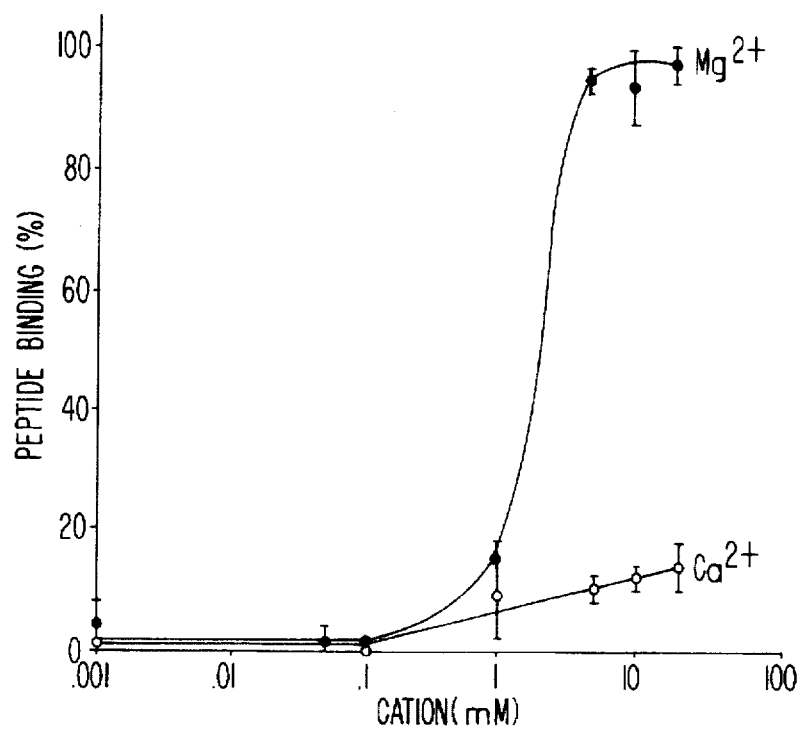
FIG. 2A and 2B show the results of $1.5\times10^5$ IMR32 cells and $1.0\times10^5$ U251 cells, respectively, incubated with increasing concentrations of $Ca^{2+}$ and $Mg^{2+}$. The results are the mean ±S.D. of three experiments done in triplicate. Nonspecific binding to IgG was subtracted from each value.

Effects of $Ca^{2+}$ and $Mg^{2+}$ on $\alpha_v\beta_1$- and $\alpha_v\beta_3$-mediated Cell Adhesion To determine whether this disparate effect of alcium on the function of these integrins held true at the ell surface, the adhesion properties of cells that expressed only one of these receptors were determined. IMR 32 cells use the $\alpha_v\beta_1$ integrin to bind to fibronectin in an RGD-dependent manner and lack other known fibronectin-binding integrins, $\alpha_5\beta_1$ and $\alpha_3\beta1$. Moreover, $\alpha_v\beta_1$ is also able to bind synthetic peptides containing the recognition sequence RGD. The IMR 32 cell adhesion to GRGDSPASSK is most likely mediated by $\alpha_v\beta_1$ because $\alpha_v\beta_1$ is the only known RGD-binding integrin on IMR 32 cells. When the adhesion of IMR 32 cells to surfaces coated with the RGD-containing peptide were measured, it was found that in the presence of $Mg^{2+}$ the IMR 32 cells adhered well to the peptide substrate (FIG. 2A), whereas $Ca^{2+}$ at concentrations up to 30 mM did not provide any significant $\alpha_v\beta_1$-mediated cell adhesion (FIG. 2A). These data parallel the binding of $\alpha_v\beta_1$ to fibronectin in receptor-loaded liposome assays. An RGD substrate was used to avoid the possibility of additional fibronectin receptors on the surface of IMR 32 cells.

Figure 2B:
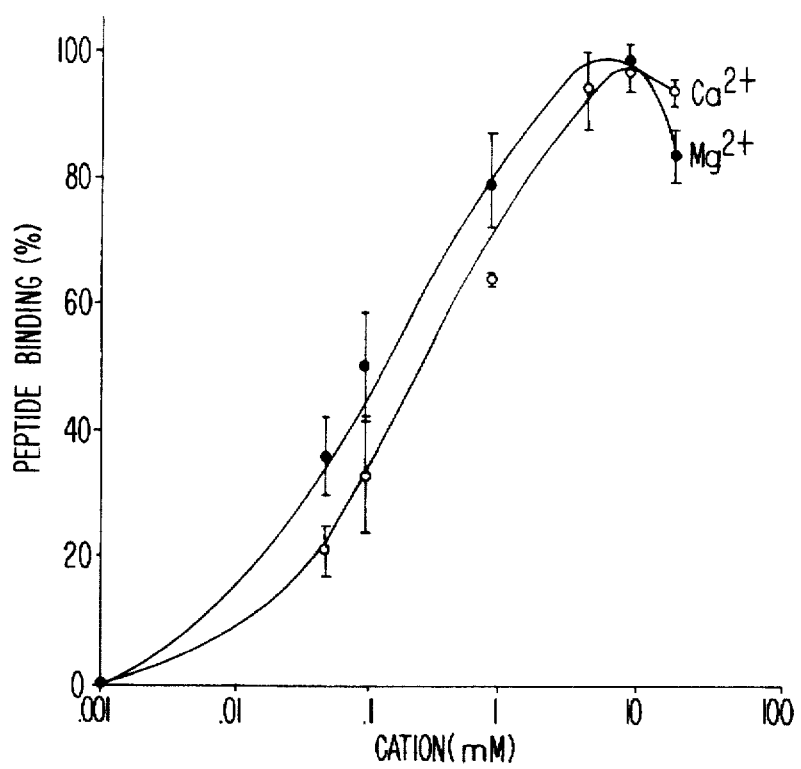

As a comparison, the adhesion of U 251 cells to GRGDSPASSK-coated (SEQ ID NO. 1) surfaces were measured. U 251 cells do not express $\alpha_v\beta_1$ on their surface, but express $\alpha_v\beta_3$. In contrast to the IMR 32 cells, the U 251 cells adhered to the peptide substrate equally well in $Ca^{2+}$ and $Mg^{2+}$ (FIG. 2B). For the U 251 as well as the IMR 32 cells, the adhesion was maximal at a cation concentration of about 5 mM and decreased at concentrations above 10 mM.

Figure 3:
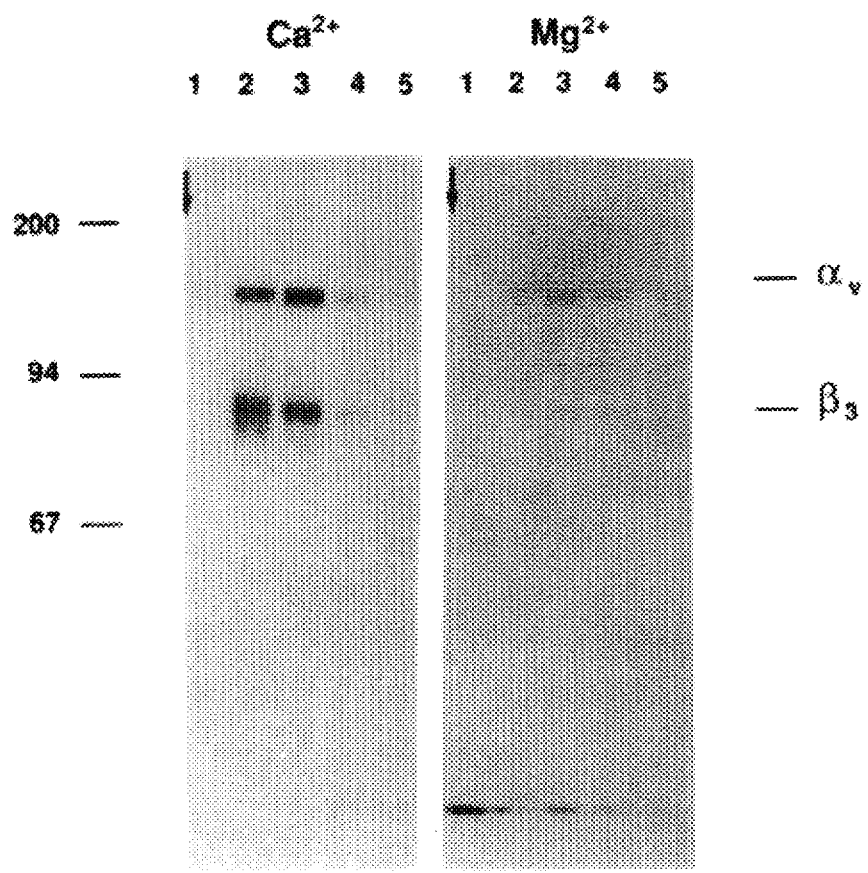
FIG. 3 shows affinity chromatography of extracts of $^{125}I$ surface-labeled U251 cells on GRGDSPK-Sepharose (SEQ ID NO. 2) in 3 mM $CaCl_2$ (left panel) or 3 mM $MgCl_2$ (right panel). The molecular mass markers are myosin (200 kDa), phosphorylase b (94 kDa), and BSA (67 kDa). The positions of the subunits $\alpha_v$ and $\beta_3$ are indicated.

To verify that the integrin mediating U 251 adhesion to RGD-peptide was $\alpha_v\beta_3$, extracts of $^{125}$I-surface-labeled U 251 cells were applied on GRGDSPK-Sepharose (SEQ ID NO. 2) in the presence of either $Ca^{2+}$ or $Mg^{2+}$. The integrin-like heterodimeric protein which was eluted from the column under both conditions migrated identically to placental $\alpha_v\beta_3$ on SDS-polyacrylamide gels (FIG. 3). Furthermore, on immunoblots, both subunits were reactive with a polyclonal anti-$\alpha_v\beta_3$ antibody, suggesting that the receptor mediating U 251 cell adhesion to RGD-peptide is identical to $\alpha_v\beta_3$. It is interesting to note that similar to the $\alpha_v\beta_3$ liposome attachment to vitronectin, $\alpha_v\beta_3$ bound better to GRGDSPK-Sepharose (SEQ ID NO. 2) in $Ca^{2+}$ than in $Mg^{2+}$ (FIG. 3).

EXAMPLE IV

Differential Isolation of $\alpha_v\beta_1$ and $\alpha_v\beta_3$

Figure 4:
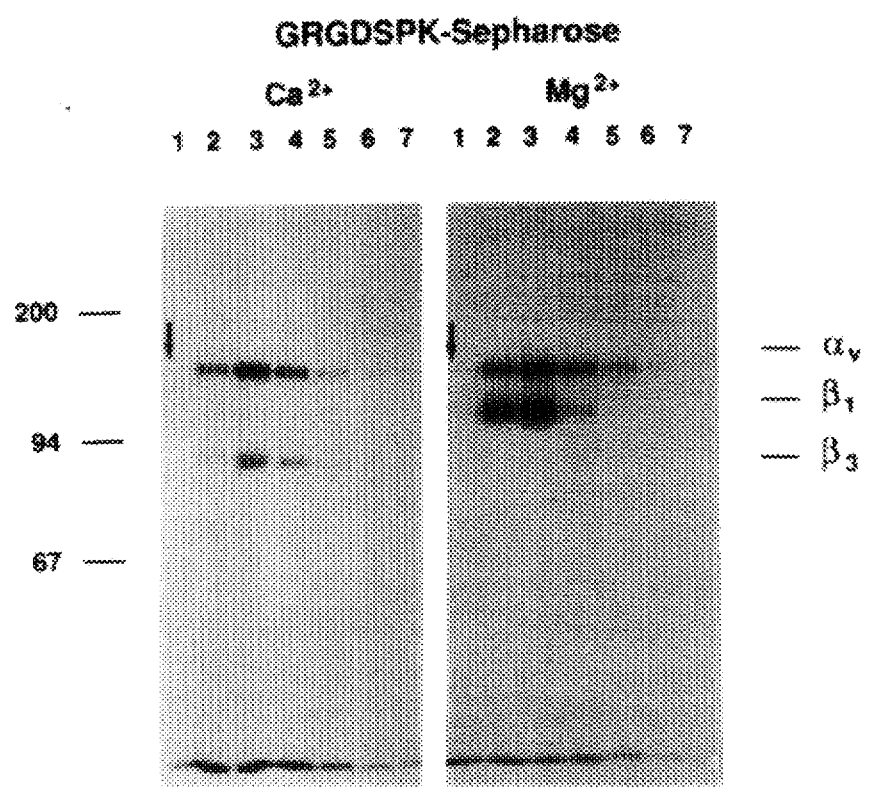
FIG. 4 shows affinity chromatography of extracts of $^{125}I$ surface labeled WI38 cells on GRGDSPK-Sepharose (SEQ ID NO. 2) in 3 mM $CaCl_2$ (left panel) or 3 mM $MgCl_2$ (right panel). The molecular mass markers are myosin (200 kDa), phosphorylase b (94 kDa), and BSA (67 kDa). The positions of the subunits $\alpha_v$, $\beta_1$ and $\beta_3$ are indicated.

WI 38 lung fibroblasts have been shown to express both $\alpha_v\beta_1$ and $\alpha_v\beta_3$ on their surface and offer a good system to study the activity of these adhesion receptors under different cation conditions simultaneously. When extracts of surface-labeled WI 38 cells supplemented with either 3 mM $Ca^{2+}$ or 3 mM $Mg^{2+}$ were applied onto two equally sized GRGDSPK-Sepharose columns (SEQ ID NO. 2), and the bound receptors were eluted with 10 mM EDTA, only $\alpha_v\beta_3$ bound to the peptide matrix in the presence of $Ca^{2+}$ (FIG. 4, left panel). No significant amounts of $\alpha_v\beta_1$ could be detected. In contrast, the predominant receptor eluted from the $Mg^{2+}$ column was $\alpha_v\beta_1$ (FIG. 4, right panel).

The main fractions from the columns run under each condition were immunoprecipitated with the following monoclonal antibodies: 147, against the av subunit (36), LM534, against the $\beta_1$ subunit and a polyclonal anti-$\beta_3$ antibody. The antibody reactivities confirmed that the receptor eluted from the $Ca^{2+}$ column was $\alpha_v\beta B_3$, and the receptor eluted from the $Mg^{2+}$ column was $\alpha_v\beta_1$. Although $\alpha_v\beta_3$ bound in $Mg^{2+}$ to its ligand, vitronectin, and to RGD-peptide in cell adhesion experiments, it did not bind appreciably to the GRGDSPK-column (SEQ ID NO. 2) under these conditions (FIG. 4, right panel). This result suggests that in $Mg^{2+}$ the affinity of $\alpha_v\beta_3$ for the peptide is low relative to that of $\alpha_v\beta_1$ for binding sites on the column. This suggestion is consistent with our finding that the $\alpha_v\beta_3$ from U 251 cells binds less efficiently to GRGDSPK-Sepharose (SEQ ID NO. 2) in $Mg^{2+}$ than in $Ca^{2+}$ (FIG. 3) as discussed above.

EXAMPLE V

Figure 5:
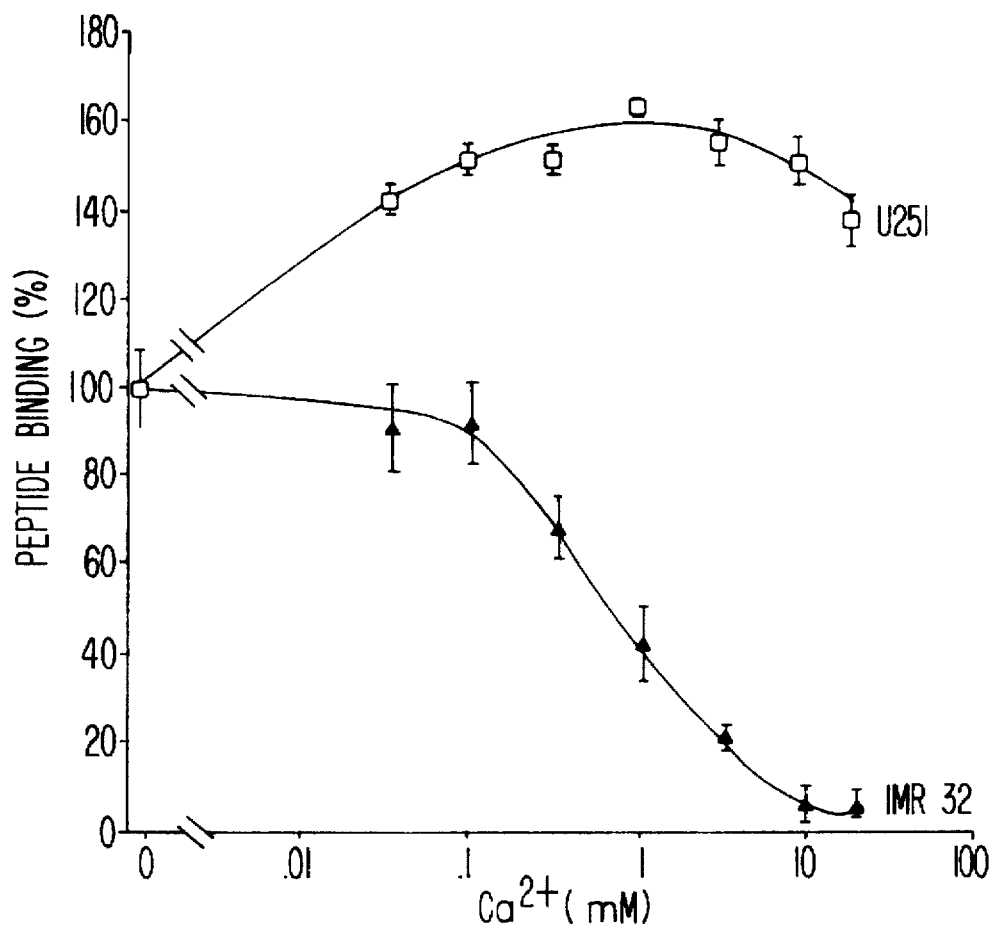
FIG. 5 shows the effects of $Ca^{2+}$ on IMR32 and U251 cell adhesion to surfaces coated with GRGDSPASSK (SEQ ID NO. 1) peptide in the presence of $Mg^{2+}$. The concentration of $Mg^{2+}$ during the 60-minute incubation period was kept constant at 5 mM, and $Ca^{2+}$ was added at increasing concentrations up to 20 mM. The cells were then solubilized with 2% SDS and quantitated by measuring the absorbance at 600 nm. The results are the mean ±S.D. of three experiments done in triplicate. Nonspecific binding to IgG was subtracted from each value. 100% adhesion was defined as the adhesion of IMR32 and U251 cells in 5 mM $Mg^{2+}$ alone without any $Ca^{2+}$ added.

Opposite Effects of $Ca^{2+}$ on $\alpha_v\beta_1$ and $\alpha_v\beta_3$ Binding in the Presence of $Mg^{2+}$ Although ineffective in the absence of $Mg^{2+}$, $Ca^{2+}$ has been shown previously to increase the binding of the leukocyte integrin LFA-1 to its ligand ICAM in the presence of $Mg^{2+}$ (Marlin et al., supra). Therefore, IMR 32 and U 251 cell adhesion to the peptide substrate were measured in increasing $Ca^{2+}$ concentrations while maintaining a constant $Mg^{2+}$ concentration. A $Mg^{2+}$ concentration of 5 mM was chosen because it provided optimal binding in liposome assays and cell adhesion for both a $\alpha_v\beta_1$ and $\alpha_v\beta_3$. Unexpectedly, $Ca^{2+}$ completely inhibited $\alpha_v\beta_1$-mediated adhesion of IMR 32 cells in a concentration-dependent manner (FIG. 5). $Ca^{2+}$ did not appear to exert any toxic effects on the cells because U 251 cell adhesion mediated by $\alpha_v\beta_3$ was significantly enhanced by all tested concentrations of calcium up to 20 mM (FIG. 5). At equal concentrations, for example, 5 mM $Mg^{2+}$ and 5 mM $Ca^{2+}$, the adhesion of IMR 32 cells was almost completely inhibited, while the adhesion of U 251 cells was enhanced by 60%.

EXAMPLE VI

The following procedures were used to obtain the results described in Examples VII to X.

A. Proteins

Bovine type I collagen was obtained from Collaborative Research Inc. (Bedford, Mass.). Human vitronectin was purified from plasma by monoclonal antibody affinity chromatography according to the methods described in Hayman et al., *PNAS (USA)* 80:4003–4007 (1983) and Suzuki et al., *J. Biol. Chem.* 259:15307–15314 (1984), which are incorporated herein by reference.

B. Cells

WI38 human lung fibroblasts were obtained from the American Type Culture Collection (ATCC No. CCL 75, Rockville, Md.). The cells were cultured in DME supplemented with 10% FCS at 37° C.

C. Antibodies

Monoclonal antibodies P1H5 and P1E6 against $\alpha_2$, PIBS against $\alpha_3$ (Wayner $\alpha_v\beta_3$ Carter, *J. Cell Biol.* 105:1873–1884 (1987)), 147 against $\alpha_v$ (Pytela et al., *Cell* 40:191–198 (1985)), AIIB2 against $\beta_1$ and BIIG2 against $\alpha_5$ (Hall et al., *J. Cell Biol.* 110:2175–2184 (1990)), control mAb 8E6 against vitronectin (Hayman et al., *PNAS (USA)* 80:4003–4007 (1983)), and polyclonal antisera to $\alpha_v\beta_3$ (Freed et al., *EMBO J.* 8:2955–2965 (1989)) were used in the various studies described herein.

D. Cell Attachment Assays

The W138 cell attachment assays were performed as previously described in Ruoslahti et al., "Fibronectin: Purification, immunochemical properties, and biological activities," *Methods of Enzymology*, S. P. Colowick $\alpha_v\beta_3$ N. O. Kaplan, eds. (Academic Press 1982), incorporated herein by reference. Briefly, $3 \times 10^4$ WI38 cells in 100 µl of TBS containing 2.5 mg/ml BSA were added to each well of microtiter plates (Titertek, Flow Laboratories, McLean, Va.) which were previously coated with 10 µg/ml of bovine type I collagen or vitronectin. $CaCl_2$ or $MgCl_2$ were added to each well at constant concentration (2.5 mM) and mixed with the cells. After 45 minutes of incubation at 37° C. in the presence of either $Mg^{2+}$ or $Ca^{2+}$, the alternate cation was added to the wells and incubated for another 45 minutes at 37° C. The unattached cells were washed away and attached cells were fixed with 3% paraformaldehyde in PBS. The cells were then stained with 0.5% toluidine blue in 3.7% formaldehyde, solubilized with 2% SDS, and the absorbance at 600 nm was measured in a vertical pathway spectrophotometer.

E. Affinity Chromatography

WI38 cells were detached with 4 mM EDTA and washed with PBS. The final cell pellet (0.6 ml) was resuspended in PBS and labeled with 3 mCi of [$^{125}$I]-sodium iodide according to the lactoperoxidase method as described in Lebien et al., *J. Immunol.* 129:2287–2292 (1982), which is incorporated herein by reference. The reaction was stopped with DME containing 0.02% sodium azide, and the cells were washed with cold PBS. The cell receptors were extracted at 4° C. for 20 minutes in TBS containing 100 mM octyl glucopyranoside (Calbiochem, La Jolla, Calif.) and 2 mM phenylmethylsulfonyl fluoride (Sigma, St. Louis, Mo.). The lysate was centrifuged at 12,000×g for 20 minutes. The supernatant was supplemented with 3 mM $MgCl_2$ and applied onto bovine type I collagen-Sepharose prepared by coupling the protein to cyanogen bromide-activated Sepharose 4B according to manufacturer's instructions (Sigma, St. Louis, Mo.). After 2 hours of incubation, the column was washed with 20 bed volumes of TBS containing 50 mM octyl glucopyranoside and 3 mM $MgCl_2$. The column was first eluted with 3 mM $CaCl_2$ and subsequently with 10 mM EDTA in TBS containing 50 mM octyl glucopyranoside and the fractions analyzed by 7.5% SDS-PAGE under nonreducing conditions and autoradiography. In similar experiments, the column was first eluted with 3 mM $Mn^{2+}$ and subsequently with $Ca^{2+}$ and EDTA as described above.

F. Immunoprecipitation

To perform immunoprecipitations, monoclonal antibodies were absorbed overnight at 4° C. onto anti-mouse IgG-agarose (Sigma). The beads were washed with TBS containing 50 mM octyl glucopyranoside, 1 mM $MgCl_2$, 1 MM $CaCl_2$, and 1 mM phenylmethylsulfonyl fluoride (wash buffer) and added to receptor fractions. After incubation for 6 hours at 4° C., the beads were washed five times with the wash buffer described above, added to SDS-PAGE sample buffer, boiled, and the eluted material was analyzed by SDS-PAGE on 7.5% gels under nonreducing conditions. The gels were dried and exposed to x-ray film (Kodak X-OMAT AR) for visualization by autoradiography.

G. Migration Assays

Migration assays were conducted using the modified Boyden Chamber as previously described in Banai et al., supra. Briefly, the chamber consists of two compartments separated by a filter, and migration is measured by counting the number of cells crossing the membrane through pores of defined size. Lower chambers were filled with modified, serum-free DME without $Ca^{2+}$, $Mg^{2+}$ or $PO_4^{3-}$. Various $CaCl_2$, $MgCl_2$, and/or EGTA concentrations as indicated in the figures were then added along with 20 ng/ml PDGF (Gibco, Grand Island, NY). Polycarbonate membrane filters of 10 micron pore size (Poretics Corp., Livermore, Calif.) that had been previously coated with 10 μg/ml of bovine type I collagen or vitronectin were then placed on top of the lower chambers, and the upper chambers were secured in place. Upper chambers were filled with $3.0 \times 10^4$ WI38 cells per chamber in the same media described above without PDGF plus the various $CaCl_2$, $MgCl_2$, and/or EGTA concentrations consistent with those in the lower chamber. In some cases, purified anti-integrin antibodies were also added to the upper chambers. Lower chamber final volumes were 27 μl and the upper chambers were 50 μl. The entire apparatus was then incubated for 3 hours at 37° C. After the incubation period, the upper chamber was removed and the filter was fixed in 3% paraformaldehyde and stained with 0.5% toluidine blue in 3.7% formaldehyde. Excess stain was washed away with water, the attached cells on the upper side of the filter were removed and the migrated cells on the underside were quantitated by counting two high-powered fields (200× magnification) per well.

Figure 6A:
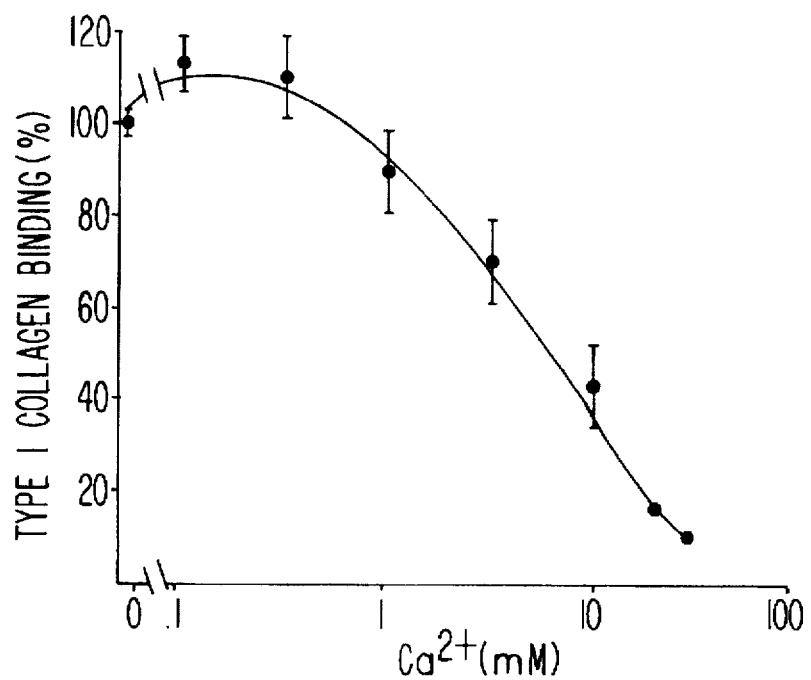
FIG. 6 illustrates the effects of $Ca^{2+}$ and $Mg^{2+}$ on the cell detachment (FIG. 6A) or attachment (FIG. 6B) of cells to surfaces coated with bovine type I collagen after initial incubation with the alternate cation in the presence of either 2.5 mM $Mg^{2+}$ or 2.5 mM $Ca^{2+}$. In detachment experiments 100% adhesion was defined as the adhesion of WI38 cells in 2.5 mM $Mg^{2+}$ alone without any $Ca^{2+}$ added. The mean absorbance at 600 nm was 0.385 ±SD. For attachment experiments (FIG. 6B), 100% was observed at 20 mM $Mg^{2+}$ after initial incubation in the presence of 2.5 mM $Ca^{2+}$. The mean absorbance at 600 nm was 0.439 ±SD. Nonspecific binding to control wells coated with 5 mg/ml BSA (2% of maximum) has been subtracted from each value.
Figure 6B:
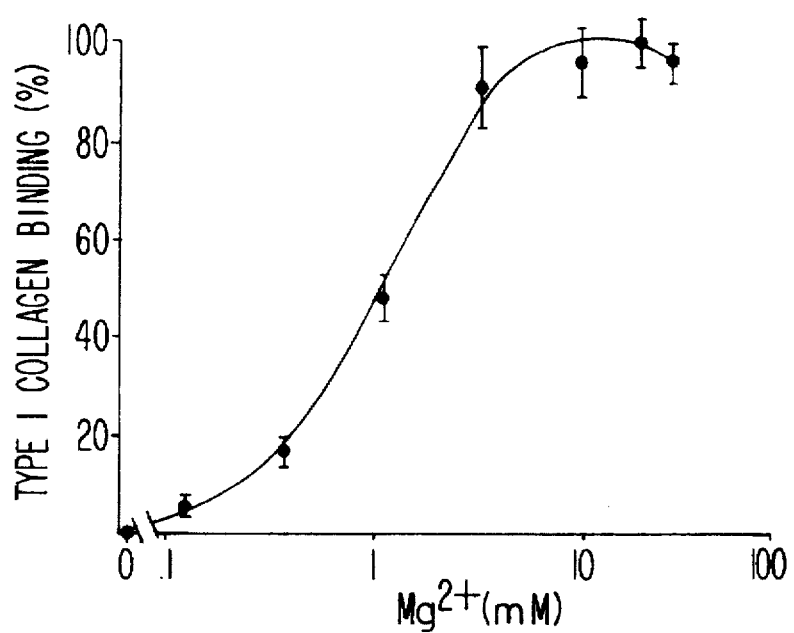

EXAMPLE VII $Ca^{2+}$ Reverses the $Mg^{2+}$-Dependent, $\alpha_v\beta_3$-Mediated Attachment of Fibroblasts to Type I Collagen Substrates The integrin profile of WI38 human fibroblasts has been shown by immunoprecipitation to include $\alpha_2\beta_1$ as described in Vogel et al., *J. Biol. Chem.* 265:5934–5937 (1990). When WI38 cells were tested for their attachment activity to bovine type I collagen in the presence of m increasing concentrations of either $Mg^{2+}$ or $Ca^{2+}$, the cells adhered well to type I collagen in the presence of $Mg^{2+}$ alone, but not at all in the presence of $Ca^{2+}$ alone. Monoclonal antibody P1E6, directed against the $\alpha_2$ integrin subunit, inhibited this $Mg^{2+}$-dependent attachment in a concentration dependent manner. It is noteworthy that maximal attachment of WI38 cells to both type I collage and vitronectin was observed in the range of 5–10 mM cation. And like the $\alpha_2\beta_1$-mediated attachment of IMR 32 cells to RGD substrates described in Example VI (D), and the $\alpha_2\beta_1$-mediated binding of platelets to collagen (Santoro, supra; and Staatz et al., supra), the attachment of W138 cells to type I collagen substrates in the presence of 2.5 mM $Mg^{2+}$, was inhibited as the $Ca^{2+}$ concentration increased. Similar results were obtained in receptor-loaded liposome binding assays with $\alpha_2\beta_1$ integrin purified from human platelets. Because the $Mg^{2+}$-dependent WI38 cell adhesion to type I collagen via $\alpha_2\beta_1$ was inhibited by $Ca^{2+}$, the detachment of cells from type I collagen by the addition of $Ca^{2+}$ was tested. As is shown in FIG. 6A, fibroblasts previously attached in $Mg^{2+}$ (2.5 mM) could be detached by the addition of $Ca^{2+}$, and the extent of this detachment was directly proportional to the increase in $Ca^{2+}$ concentration. To test whether this effect of $Ca^{2+}$ was detrimental to the cells, the reverse experiment was conducted in which cells were first incubated in the presence of $Ca^{2+}$ (2.5 mM), and subsequently exposed to an increasing $Mg^{2+}$ titration. While no attachment was observed on type I collagen in the presence of $Ca^{2+}$ alone, subsequent addition of increasing concentrations of $Mg^{2+}$ yielded a proportional increase in attachment (FIG. 6B).

Figure 7:
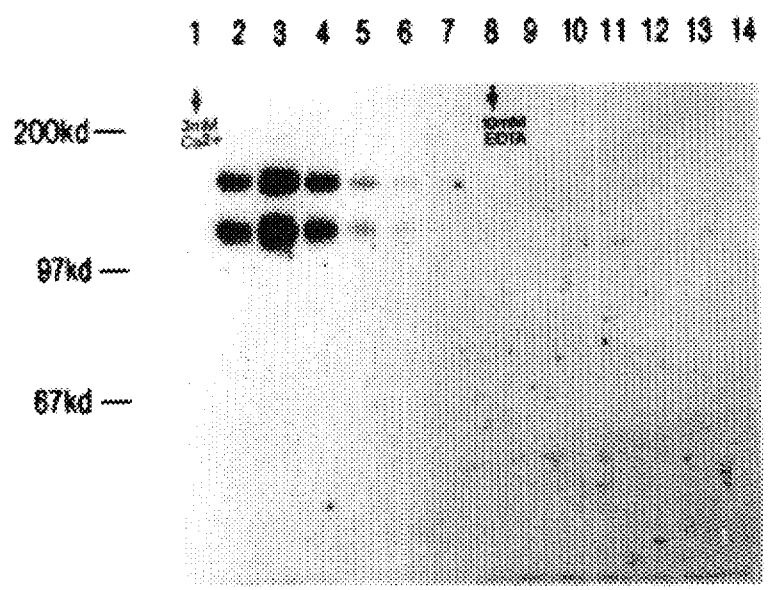
FIG. 7A illustrates affinity chromatography of extracts of $[^{125}I]$ surface labeled WI38 cells on bovine type I collagen-Sepharose. Extracts of surface-iodinated WI38 cells were supplemented with 3 mM $MgCl_2$ and applied onto a 1.0 ml collagen-Sepharose column. After washing with wash buffer (see materials and methods) containing 3 mM $Mg^{2+}$, the column was eluted with 3 mM $Ca^{2+}$ followed by 10 mM EDTA.
FIG. 7B shows the results of immunoprecipitation experiments of eluted material from lanes 2–4 of FIG. 7A using monoclonal antibodies P1H5 against $\alpha_2$, P1B5 against $\alpha_3$, 147 against $\alpha_v$, and 8E6 against vitronectin. The molecular mass markers were myosin (200 kD), phosphorylase b (98 kD), and BSA (67 kD). The positions of the subunits $\alpha_2$ and $\beta_1$, are indicated.

EXAMPLE VIII $Ca^{2+}$ Elutes the $\alpha_2\beta_1$ Integrin From Bovine Type I Collagen-Sepharose To study this apparent reversibility in cation-dependent adhesion further, surface [$^{125}$I]-labeled WI38 membrane extracts supplemented with 3 mM $Mg^{2+}$ were chromatographed over bovine type I collagen-Sepharose and the column was subsequently eluted with 3 mM $Ca^{2+}$. As is shown in FIG. 7A, all of the bound integrin was eluted from the column with $Ca^{2+}$. Subsequent elution with 10 mM EDTA released no additional receptor. FIG. 7B shows by immunoprecipitation with various monoclonal antibodies described in Example VI(C) that the integrin eluted was indeed $\alpha_2\beta_1$. After extensive dialysis back into 3 mM $Mg^{2+}$, this purified receptor rebound to the column and was, again, eluted with $Ca^{2+}$. In a reverse experiment in which WI38 extracts supplemented with 3 mM $Ca^{2+}$ were chromatographed over GRGDSPK-Sepharose (SEQ ID NO. 2), $\alpha_v\beta_3$ bound to the column and could not be eluted with 3 mM $Mg^{2+}$. Elution could only be achieved with EDTA.

To confirm that the elution of $\alpha_2\beta_1$ was due to the addition of $Ca^{2+}$ and not the removal of $Mg^{2+}$, two additional experiments were undertaken. $Mg^{2+}$-supplemented WI38 extracts were loaded onto a type I collagen-Sepharose column and eluted first with $Mg^{2+}$, then $Ca^{2+}$. Again, all of the integrin was released with $Ca^{2+}$, while none was eluted with $Mg^{2+}$. WI38 extracts supplemented with 1 mM $Mg^{2+}$ were also loaded onto a type I collagen-Sepharose column and eluted with 4 mM $Mg^{2+}$, 3 mM $Mg^{2+}$ plus 1 mM $Ca^{2+}$, and finally EDTA. The change to 4 mM $Mg^{2+}$ caused no integrin to be released. However, when 3 mM $Mg^{2+}$ plus 1 mM $Ca^{2+}$ was introduced, the integrin was eluted, clearly indicating that $Ca^{2+}$ reverses the $Mg^{2+}$-dependent binding of $\alpha_2\beta_1$ to type I collagen. It is noteworthy that the detachment by $Ca^{2+}$ of cells previously bound in $Mg^{2+}$ (FIG. 6A) correlates well with this affinity chromatography result in that $Ca^{2+}$ appears to weaken the $Mg^{2+}$-dependent integrin-ligand interactions. It has also been found that $Ca^{2+}$ can elute both $\alpha_2\beta_1$ from fibronectin-Sepharose when this integrin has been bound to the column from Mg2+ supplemented WI38 extracts, and $\alpha_v\beta_1$ from RGD-Sepharose bound from $Mg^{2+}$-supplemented IMR 32 extracts.

EXAMPLE IX

Figure 8A:
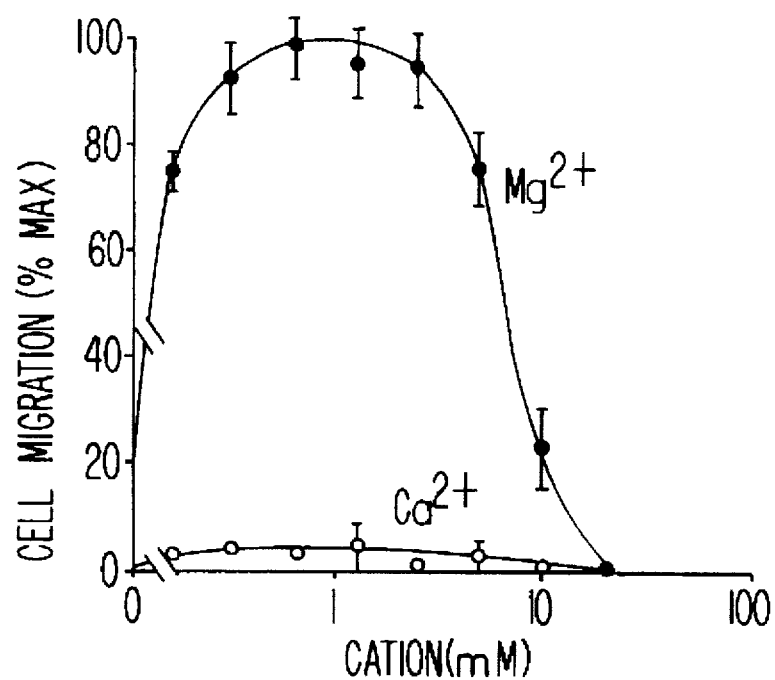
FIG. 8 illustrates the effects of $Ca^{2+}$ and $Mg^{2+}$ on fibroblast migration through ligand-coated filters in the presence of various concentrations of $Ca^{2+}$ (O) or $Mg^{2+}$ (●). The filters were coated with 10 µg/ml bovine type I collagen (FIG. 8A) or vitronectin (FIG. 8B). After incubation, filters were fixed in methanol and stained with Diff-Quik Solution II (Scientific Products, McGraw Park, Ill.). After rinsing, adherent cells were removed from the upper side of the filter and migrated cells on the underside were counted by taking the mean of two high-powered fields (200× magnification) per well using an inverted, light microscope (Olympus CK 2). The results represent the mean ±SD of three experiments done in triplicate. Migration on type I collagen and the control, vitronectin, are compared to each other and all values are expressed as a percentage of maximum migration (68 cells ±SD/high-powered field), which was observed on type I collagen. No migration was observed in the absence of divalent cations.
Figure 8B:
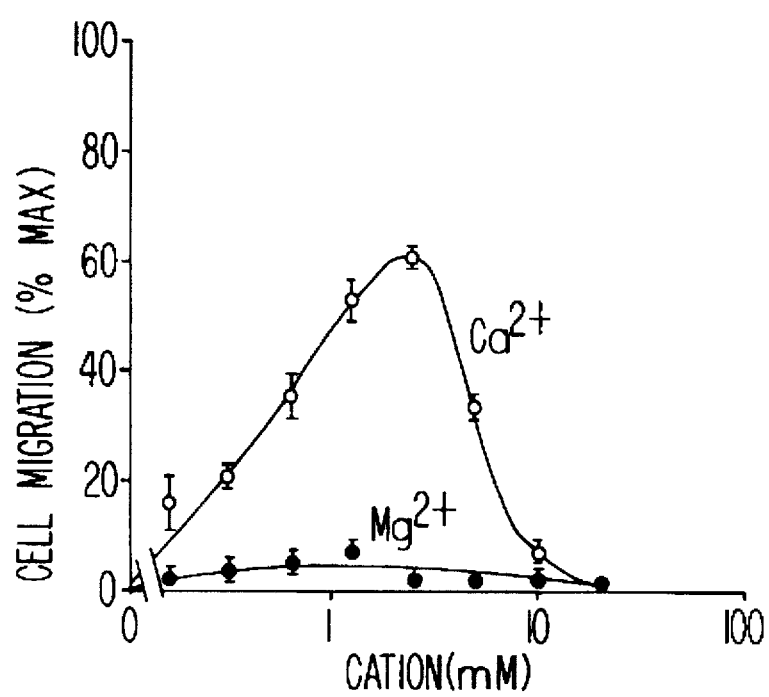
Figure 9A:
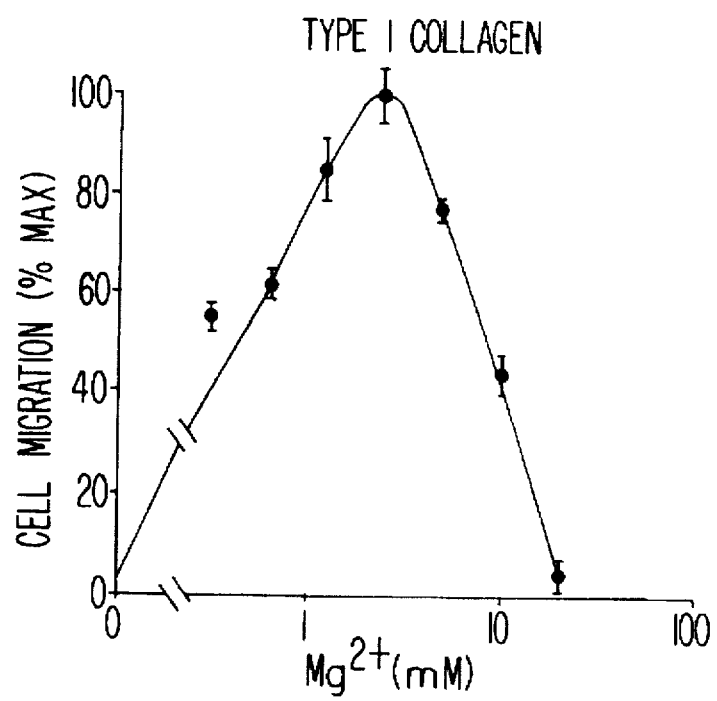
FIG. 9 illustrates the combined effects of $Ca^{2+}$ and $Mg^{2+}$ on fibroblast migration on type I collagen. Migration was determined and quantitated as described in FIG. 3 with 1.5 mM $Ca^{2+}$ (FIG. 9A) or $Mg^{2+}$ (FIG. 9B) plus a titration of the alternate cation on type I collagen (10 µg/ml) coated filters. The results represent the mean ±SD of three experiments done in triplicate. 100% (mean=145 cells ±SD/high-powered field) was observed at 2.5 mM $Mg^{2+}$/1.5 mM $Ca^{2+}$ (FIG. 9A), and at 1.5 mM $Mg^{2+}$/1.25 mM $Ca^{2+}$ (FIG. 9B). No migration was observed in the absence of divalent cations.
Figure 9B:
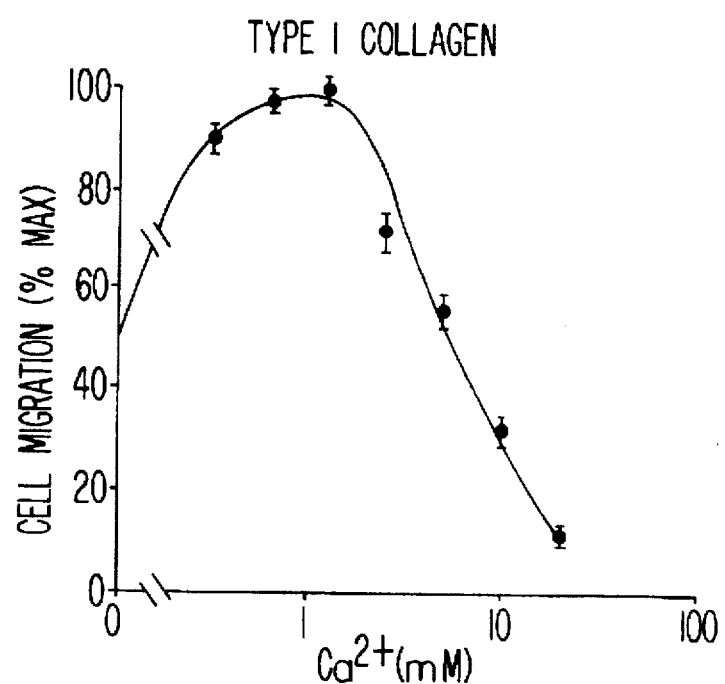
Figure 10:
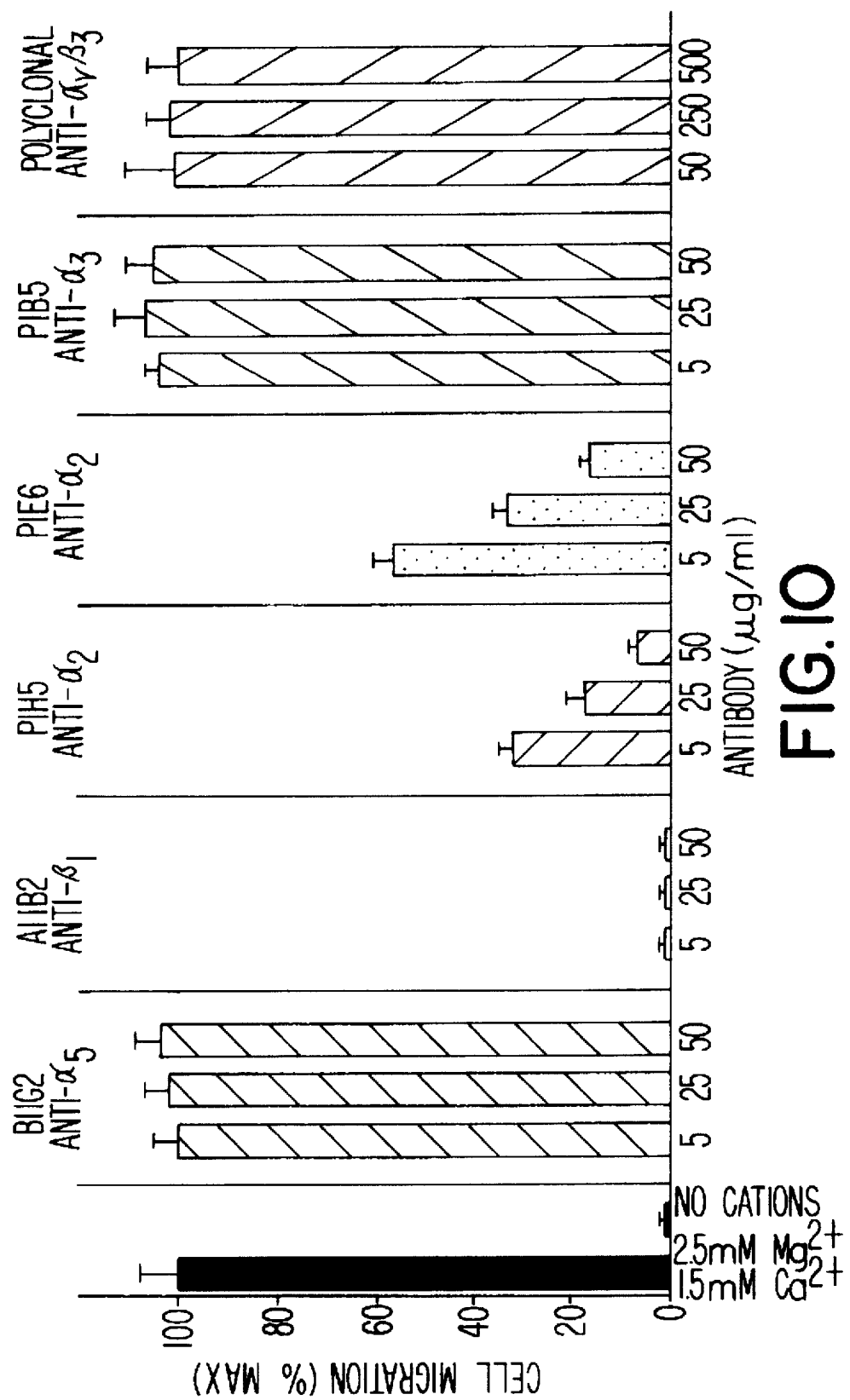
FIG. 10 shows the effects of inhibitory anti-integrin monoclonal/polyclonal antibodies on WI38 fibroblast migration on type I collagen. Migration was determined and quantitated in the presence of 2.5 mM $Mg^{2+}$/1.5 mM $Ca^{2+}$ and the indicated purified antibody concentrations. 100% (mean=150 cells ±SD/high-powered field) is defined as that observed with 2.5 mM $Mg^{2+}$/1.5 mM $Ca^{2+}$ without any antibody. The results represent the mean ±SD of two experiments done in duplicate. No migration was observed in the absence of divalent cations.

Elevated Extracellular $Mg^{2+}$ Enhances $\alpha_2\beta_1$ Integrin-Mediated Fibroblast Migration on Type I Collagen The attachment/detachment data together with the affinity chromatography results suggest that $Ca^{2+}$ and $Mg^{2+}$ are involved in the modulation of integrin function, for example, in mediating a cellular process such as migration. In modified Boyden chamber migration assays, WI38 fibroblasts were migratory on type I collagen in $Mg^{2+}$ and not in $Ca^{2+}$ (FIG. 8A). However, a two-fold enhancement of migration was observed when these cations were utilized in combination, with maximum migration observed when $Mg^{2+}/Ca^{2+}$ ratios were higher than one (FIG. 9A–B). Specifically, FIG. 9B shows that in the presence of 1.5 mM $Mg^{2+}$ without $Ca^{2+}$, migration is about half that observed when optimal combinations of the two cations are utilized. As a control, WI38 cells migrated on vitronectin substrates in the presence of $Ca^{2+}$ alone but, not in $Mg^{2+}$ (FIG. 8B), indicating that the β3 integrin has different cation equirements for the promotion of migration versus dhesion. It should be noted that maximal migratory ctivity is achieved at significantly lower combined divalent cation concentrations (<4 mM) than maximal adhesion (5–10 mM) in a single cation. Light micrographs were made to determine the relative comparison between the maximum fibroblast migration observed on type I collagen substrates in $Ca^{2+}$ alone, $Mg^{2+}$ alone, and in combination with slight excess of $Mg^{2+}$.

The micrographs illustrate that at 1.25 mM $Ca^{2+}$, there are virtually no cells present on the type I collagen coated plates. At 1.25 mM $Mg^{2+}$, there are cells present and appear to attach and spread with visible nuclei. In combination with optimal $Mg^{2+}/Ca^{2+}$ ratios of 2.5 mM/1.5 mM, the cells appear similar to those of $Mg^{2+}$ only, except that there are about twice as many (i.e., a two-fold increase). In controls without divalent cations, there is no adhesion or migration.

Because migration was enhanced when the two cations were present together, it is questionable whether the migration observed in the presence of $Mg^{2+}$ alone is dependent on the efflux of $Ca^{2+}$ from the cell. This dependency seems unlikely because no migration was observed without the addition of cations, even after a 3 hour incubation on either type I collagen or the control ligand, vitronectin, which exhibits migratory activity in $Ca^{2+}$ alone (FIG. 8B). Moreover, the addition of 5 mM EGTA to wells containing 3 mM $Mg^{2+}$ reduced fibroblast migration on type $Ca^{2+}$ collagen substrates by only about 25% of that observed in the presence of 3 mM $Mg^{2+}$ alone, but completely abolished migration on vitronectin substrates in the presence of 3 mM $Ca^{2+}$. Although not intending to be limited to any particular theory for the observation, the observed non-specific chelation of $Mg^{2+}$ by EGTA is the likely explanation for the observed reduction in migration on collagen.

EXAMPLE X

Antibodies Directed Against the Integrin $\alpha_2$ and $\beta_1$ Subunits Inhibit Fibroblast Migration on Type I Collagen Monoclonal antibodies directed against various integrin subunits were tested for inhibitory activity of migration under the optimal conditions of 2.5 mM Mg2+/1.5 mM $Ca^{2+}$ (FIG. 9A). As is shown in FIG. 6, P1H5 and P1E6, directed against the $\alpha 2$ subunit, and AIIB2, directed against the $\beta_1$ subunit, essentially completely inhibited WI38 fibroblast migration on type I collagen. No inhibition was observed in the presence of equivalent concentrations of P1B5 directed against the $\alpha_3$ subunit, BIIG2 directed against the $\alpha 5$ subunit or a polyclonal antiserum directed against $\alpha_v \beta_3$. In control migration studies on vitronectin, laminin and fibronectin, the antibodies showing no inhibition on type I collagen were functional blockers on their respective ligand. Thus, it appears that the integrin $\alpha_2 \beta_1$ is the target of the divalent cation effects described herein.

Although the invention has been described with reference to the disclosed embodiments, it should be understood that various modifications can be made without departing from the spirit of the invention. Accordingly, the invention is limited only by the following claims.

---

We claim:

1. A method for enhancing the migration of an integrin-expressing cell, comprising increasing the extracellular $Mg^{2+}/Ca^{2+}$ concentration ratio in contact with said cell to greater than 1 to enhance the migration of said cell, wherein the combined $Mg^{2+}$ and $Ca^{2+}$ concentration is less than 4 mM.

2. The method of claim 1, wherein said cell expresses a type I collagen integrin.

3. The method of claim 2, wherein said integrin is $\alpha_2\beta_1$.

4. The method of claim 1, wherein said cell expresses $\alpha_2\beta_1$.

5. The method of claim 1, wherein said enhanced migration promotes wound healing.

6. The method of claim 1, wherein said extracellular $Mg^{2+}/Ca^{2+}$ concentration ratio is in the range of about 1.5 to 2.

7. The method of claim 1, wherein said combined $Mg^{2+}$ and $Ca^{2+}$ concentration is in the range of about 2 mM to 3 mM.

* * * * *

UNITED STATES PATENT AND TRADEMARK OFFICE
CERTIFICATE OF CORRECTION

PATENT NO. : 5,759,855  
DATED : June 2, 1998  
INVENTOR(S) : Pierschbacher et al.

Page 1 of 2

It is certified that error appears in the above-identified patent and that said Letters Patent is hereby corrected as shown below:

Column 1,  
Lines 49 and 53, please delete "a subunits" and replace therefor with -- α subunits --.

Column 2,  
Line 3, please delete the carriage return at the end of the line.

Column 7,  
Line 21, please delete "any a" and replace therefor with -- any --.

Column 8,  
Lines 6 and 8, please delete "a subunit" and replace therefor with -- α subunit --.  
Line 51, please delete the carriage return at the end of the line.  
Line 54, please delete "to α" and replace therefor with -- to a --.

Column 10,  
Lines 7 and 12, please delete "a subunit," and replace therefor with -- α subunit --.

Column 12,  
Line 49, please delete "144:4750489" and replace therefor with -- 144:475-489 --.

Column 13,  
Line 58, please delete "$a_v\beta_3$" and replace therefor with -- $a_v\beta_1$ --.

Column 14,  
Line 9, please delete "alcium" and replace therefor with -- calcium --.  
Line 10, please delete "the ell" and replace therefor with -- the cell --.  
Line 15, please delete "$a_v\beta1$" and replace therefor with -- $a_v\beta_1$ --.

Column 15,  
Line 1, please delete "av" and replace therefor with -- $a_v$ --.  
Line 4, please delete "$a_v\beta B_3$" and replace therefor with -- $a_v\beta_3$ --.  
Line 56, please delete "PIBS" and replace therefor with -- P1B5 --.

Column 16,  
Line 51, please delete "CaC12" and replace therefor with -- $CaCl_2$ --.

Column 17,  
Line 24, please delete "$Mg^2$+-Dependent," and replace therefor with -- $Mg^{2+}$-Dependent, --.

UNITED STATES PATENT AND TRADEMARK OFFICE
CERTIFICATE OF CORRECTION

PATENT NO.    : 5,759,855
DATED         : June 2, 1998
INVENTOR(S)   : Pierschbacher et al.

It is certified that error appears in the above-identified patent and that said Letters Patent is hereby corrected as shown below:

<u>Column 17,</u>
Line 31, please delete "m increasing" and replace therefor with -- increasing --.

<u>Column 18,</u>
Line 59, please delete "equire-" and replace therefor with -- require --.
Line 60, please delete "dhesion." and replace therefor with -- adhesion --.
Line 61, please delete "ctivity" and replace therefor with -- activity --.

Signed and Sealed this

Second Day of October, 2001

Attest:

NICHOLAS P. GODICI
*Attesting Officer*          *Acting Director of the United States Patent and Trademark Office*